United States Patent [19]

Hughes

[11] Patent Number: 5,124,322
[45] Date of Patent: Jun. 23, 1992

[54] DIPEPTIDE COLLAGENASE INHIBITORS

[75] Inventor: Ian Hughes, Harlow, England

[73] Assignee: Beecham Group p.l.c., Middlesex, England

[21] Appl. No.: 367,961

[22] Filed: Jun. 19, 1989

[30] Foreign Application Priority Data

Jun. 22, 1988 [GB] United Kingdom ............... 8814813

[51] Int. Cl.⁵ ................. A61K 31/395; A61K 31/16; C07D 225/00; C07D 235/34
[52] U.S. Cl. ........................ 514/183; 540/1; 540/544; 540/575; 540/533; 544/54; 544/584; 544/88; 544/157; 546/192; 546/336; 546/164; 548/495; 549/13; 549/23; 549/58; 549/65; 549/407; 549/486; 549/487; 549/493; 560/17; 562/426; 562/431; 564/154; 514/618; 514/616; 514/540; 514/218; 514/513; 514/456; 514/459; 514/466; 514/471; 514/542; 514/562; 514/331; 514/238.2; 514/226.8; 514/227.5; 514/419; 514/357; 514/311; 558/254
[58] Field of Search ............... 564/154; 514/618, 183, 514/218, 616, 540, 513, 357, 311, 432, 443, 438, 456, 459, 466, 471, 419, 238.2, 226.8, 227.5, 542, 562; 558/254; 540/544, 575, 553, 1; 546/192, 336, 164; 544/88, 54, 58.4, 159; 549/23, 13, 58, 65, 467, 466, 462, 493; 560/17; 561/131, 426

[56] References Cited

U.S. PATENT DOCUMENTS 4,595,700 6/1986 Donald et al. ............ 514/616
4,623,729 11/1986 Natarajan et al. .......... 564/154
4,937,243 6/1990 Markwell et al. .......... 514/616

FOREIGN PATENT DOCUMENTS 8806890 9/1988 World Int. Prop. O. .

Primary Examiner—Richard L. Raymond
Assistant Examiner—Mark Russell
Attorney, Agent, or Firm—Hopgood, Calimafde, Kalil, Blaustein & Judlowe

[57] ABSTRACT

Novel compounds of formula (I), salts, solvates and hydrates thereof:

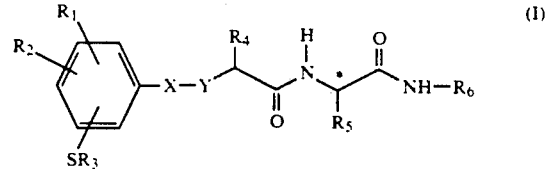

in which:
$R_1$ and $R_2$ are independently hydrogen; alkyl; alkoxy; halogen; or $CF_3$;
$R_3$ is hydrogen; acyl, such as

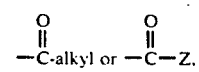

where Z is optionally substituted aryl; or a group R—S— where R is an organic residue such that the group R—S— provides an in vivo-cleavable disulphide bond;
$R_4$ is $C_{3-6}$ alkyl;
$R_5$ is hydrogen; alkyl; —$CH_2$—$R_{10}$ where $R_{10}$ is optionally substituted phenyl or heteroaryl; or a group

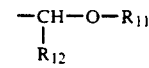

where $R_{11}$ is hydrogen; alkyl; or —$CH_2$—Ph is optionally substituted phenyl; and $R_{12}$ is hydrogen or alkyl; and
$R_6$ is hydrogen; alkyl; or a group

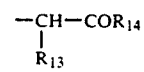

where $R_{13}$ is hydrogen; or alkyl; and $R_{14}$ is hydroxy; alkoxy; or —$NR_{7a}R_8$ where each of $R_{7a}$ and $R_8$ is hydrogen or alkyl, or $R_{7a}$ and $R_8$ together with the nitrogen atom to which they are bonded form a 5-, 6- or 7- membered ring with an optional oxygen, sulphur or optionally substituted nitrogen atom in the ring; or
$R_5$ and $R_6$ are joined together as —$(CH_2)_m$— where m is an integer from 4 to 12;
X is $(CH_2)_n$ where n is 0, 1, or 2; and Y is $CH_2$, processes for their preparation and their use as collagenase inhibitors.

14 Claims, No Drawings

DIPEPTIDE COLLAGENASE INHIBITORS

The present invention relates to novel thiophenol derivatives, processes for their preparation and their use in medicine. In particular, the present invention relates to their use as collagenase inhibitors for treating arthritic and other diseases.

The range of therapeutic applications of the collagenase inhibitors described hereinafter reflects the fundamental role of collagen within the connective tissue matrix throughout the body, and extends to many diseases not primarily due to collagen destruction but involving tissue remodelling, as these will also be susceptible to clinical intervention with collagenase inhibitors. In particular, inhibition of collagenases released from synovial and skin fibroblasts, chondrocytes, peripheral mononuclear cells, keratinocytes and gingival tissue, as well as inhibition of collagenase stored in polymorphonuclear leucocytes (PMNLs) should be of therapeutic value, and the present compounds are envisaged as having application against these and related mammalian collagenases, and related neutral metalloproteases.

Specifically, collagenase inhibitors will provide useful treatments for arthritic diseases such as rheumatoid arthritis and osteoarthritis, soft tissue rheumatism, polychondritis and tendonitis; for bone resorption diseases such as osteoporosis, Paget's disease, hyperparathyroidism and cholesteatoma; for the recessive classes of dystrophic epidermolysis bullosa; for periodontal disease and related consequences of gingival collagenase production or of PMNL collagenase production following cellular infiltration to inflamed gingiva; for corneal ulceration e.g. that induced by alkali or other burns, by radiation, by vitamin E deficiency or retinoid deficiency; and for systemic chemotherapy of cancer, where collagenase has been implicated in the neovascularization required to support tumour survival and growth, and in the penetration of tumour cells through the basement membrane of the vascular walls during metastasis. A collagenase inhibitor may also be of use in some post-operative conditions such as colonic anastomosis in which collagenase levels are raised.

As a particular example of the therapeutic value of collagenase inhibitors, chronic arthritic diseases lead to extensive loss of the collagen and proteoglycan components within the cartilage and bone of the affected joints. Neutral metalloproteases, especially collagenases, proteoglycanases (stromelysins) and gelatinases, are currently thought to be the major enzymes involved.

These enzymes, and other enzymes active in the collagenase family, have been detected in extracts of synovial and cartilage tissue, and have also been extensively studied in tissue cultures of these organs. Apart from control of the biosynthesis or secretion of the enzymes, the most significant natural regulation of the activity of collagenase and proteoglycanase in the normal and diseased state, is considered to be the production of inhibitors such as the Tissue Inhibitor of Metalloproteases (TIMP) and $\alpha_2$-macroglobulin. An imbalance between the levels of proteolytic enzymes and natural inhibitors will allow destruction of the connective tissue components to proceed.

Restoration of the enzyme-inhibitor balance by treatment with synthetic inhibitors of collagenase thus offers a useful therapy for a wide range of connective tissue diseases in which collagenolytic activity is a causative or major contributory factor.

U.S. Pat. No. 4,595,700 (Searle) discloses compounds of the formula (A):

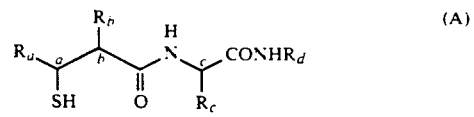

in which:

$R_a$ represents lower alkyl, phenyl or phenyl lower alkyl;

$R_b$ and $R_d$ represent lower alkyl; and $R_c$ represents lower alkyl, benzyloxyalkyl, alkoxybenzyl or benzyloxybenzyl wherein the oxyalkyl or alkoxy moiety contains 1 to 6 carbon atoms and a, b and c represent chiral centres with optional R or S stereochemistry.

These compounds are described as inhibitors of collagenase, useful in the treatment of rheumatoid arthritis and related diseases in which collagenolytic activity is a contributing factor.

A novel class of thiophenol derivatives has now been discovered, which are collagenase inhibitors and thus of potential utility in the treatment of diseases in which collagenolytic activity and tissue remodelling is implicated.

According to the present invention there is provided a compound of general formula (I), or a salt, solvate or hydrate thereof:

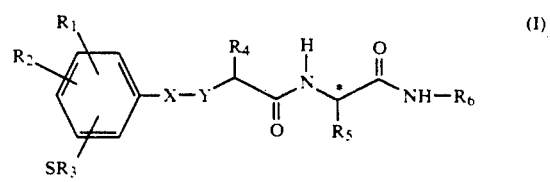

in which:

$R_1$ and $R_2$ are independently hydrogen; alkyl; alkoxy; halogen; or $CF_3$;

$R_3$ is hydrogen; acyl, such as

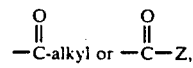

where Z is optionally substituted aryl; or a group R—S— where R is an organic residue such that the group R—S— provides an in vivo-cleavable disulphide bond;

$R_4$ is $C_{3-6}$ alkyl;

$R_5$ is hydrogen; alkyl; —$CH_2$—$R_{10}$ where $R_{10}$ is optionally substituted phenyl or heteroaryl; or a group

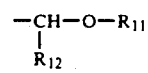

where $R_{11}$ is hydrogen; alkyl; or —$CH_2$—Ph where Ph is optionally substituted phenyl; and $R_{12}$ is hydrogen or alkyl; and $R_6$ is hydrogen; alkyl; or a group

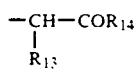

where $R_{13}$ is hydrogen; or alkyl; and $R_{14}$ is hydroxy; alkoxy; or $-NR_{7a}R_8$ where each of $R_{7a}$ and $R_8$ is hydrogen or alkyl, or $R_{7a}$ and $R_8$ together with the nitrogen atom to which they are bonded form a 5-, 6- or 7-membered ring with an optional oxygen, sulphur or optionally substituted nitrogen atom in the ring;

or $R_5$ and $R_6$ are joined together as $-(CH_2)_m-$ where m is an integer from 4 to 12;

X is $(CH_2)_n$ where n is 0, 1, or 2; and Y is $CH_2$.

Unless otherwise specified, each alkyl or alkoxy group is a $C_{1-8}$ group, more preferably $C_{1-6}$, and may be a straight chain or branched.

Optional substituents for aryl and heteroaryl groups may be selected from OH, $C_{1-6}$ alkyl, $C_{1-6}$ alkoxy and halogen.

Values for $R_1$ and $R_2$ include hydrogen, $C_{1-4}$ alkyl especially methyl, $C_{1-4}$ alkoxy especially methoxy, halogen especially chlorine, and $CF_3$. Preferably both $R_1$ and $R_2$ are hydrogen or one of $R_1$ and $R_2$ is hydrogen and the other is $C_{1-4}$ alkyl especially methyl, $C_{1-4}$ alkoxy especially methoxy, halogen especially chlorine, or $CF_3$.

When $R_3$ is

is preferably an optionally substituted phenyl group.

$R_3$ is preferably hydrogen.

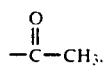

benzoyl, or a group $R-S-$ where R is a $C_{1-6}$ alkyl group or such that the compound of formula (I) is a dimer about the disulphide bond. An $R_3$ hydrogen is especially preferred.

$R_4$ is preferably a $C_4$ alkyl group, such as n-butyl, iso-butyl or sec-butyl, especially iso-butyl.

When $R_5$ is $-CH_2-R_{10}$ and $R_{10}$ is heteroaryl, values for $R_{10}$ include 5- or 6- membered monocyclic and 9- or 10-membered bicyclic heteroaryl of which 9- or 10-membered bicyclic heteroaryl is preferred.

In addition, 5- or 6- membered monocyclic and 9- or 10-membered bicyclic heteroaryl preferably contain one or two heteroatoms selected from nitrogen, oxygen and sulphur. When $R_{10}$ is 9- or 10- membered bicyclic heteroaryl the two rings are preferably fused with one 5- or 6-membered ring containing a single heteroatom, for example indolyl.

$R_5$ is preferably iso-butyl; benzyl; or $C_{1-6}$ alkoxybenzyl, such as 4-methoxybenzyl; 1-(benzyloxy)ethyl; or 9- or 10- membered fused bicyclic heteroarylmethyl such as 3-indolylmethyl.

Values for $R_6$ include hydrogen; alkyl, such as methyl or ethyl, preferably methyl; and 1-(methoxycarbonyl)ethyl.

When groups $R_5$ and $R_6$ are combined as $-(CH_2-)_m-$, an especially favourable form is where m=10, resulting in a lactam structure based on a 13-membered ring.

n is preferably zero.

The compounds of formula (I) may form salts with bases e.g. sodium hydroxide. When a basic nitrogen atom is present, the compounds of formula (I) may form acid addition salts e.g. with hydrochloric acid. Such compounds form part of the present invention.

Where compounds of formula (I), or salts thereof, form solvates such as hydrates, these also form an aspect of the invention.

The compounds of formula (I) have at least one asymmetric centre and therefore exist in more than one stereoisomeric form. The invention extends in all such forms and to mixtures thereof, including racemates, and diastereoisomeric mixtures.

Preferred isomers are those having the S configuration at the chiral centre marked with an asterisk in formula (I), when $R_5$ is other than hydrogen.

The compounds of formula I or their salts, solvates or hydrates are preferably n pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% by weight, preferably 75%, more preferably 90% and still more preferably 95% or 99% or more of the compound of formula I or its salt or solvate.

One preferred pharmaceutically acceptable form is the crystalline form.

The present invention provides the compounds of formula (I) or pharmaceutically acceptable salts or solvates thereof for use as active therapeutic agents, particularly as agents for treatment of musculo-skeletal disorders resulting from collagenolytic activity, particularly arthritic diseases, and tissue remodelling, and also for the systemic chemotherapy of cancer.

The present invention also provides a process for the preparation of a compound of formula (I) in which $R_3$ is hydrogen, which comprises cleaving a group P from a compound of formula (II):

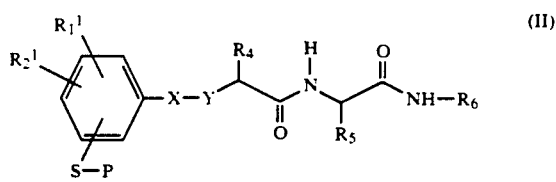

wherein P is $P_1$ which is a conventional sulphur protecting group or $P_2$ which is a group $R'-S-$ where R' is any organic residue such that the group $R'-S-$ provides a cleavable disulphide bond, $R_1^1$ and $R_2^1$ are $R_1$ and $R_2$ respectively as defined for formula (I) or groups convertible thereto, and $R_4$, $R_5$, $R_6$, X and Y are as defined for formula (I), and thereafter, as required, converting $R_1^1$ to $R_1$ and $R_2^1$ to $R_2$.

Typically a protecting group $P_1$ is an optionally substituted benzyl group, such as benzyl or alkoxybenzyl e.g. 4-methoxybenzyl, an aliphatic or aryl acyl group such as acetyl or benzoyl, or a tertiary butyl group. When $P_1$ is acyl it is of course identical to $R_3$, and so compounds of formula (II) in which $R_1^1$ is $R_1$, $R_2^1$ is $R_2$ and P is acyl are themselves compounds of the invention.

When $P_1$ is a tertiary butyl group or a substituted benzyl sulphur protecting group, such as 4-methoxybenzyl, then $P_1$ may be removed by treatment with mercuric acetate in trifluoroacetic acid containing anisole followed by reaction with hydrogen sulphide in dimethyl formamide, in a procedure analogous to that described in Chem. Pharm. Bull [1978], 26, 1576.

When $P_1$ is an acyl group it may be removed by treatment with a base, for example aqueous ammonia or dilute aqueous sodium hydroxide, or by treatment with an acid, for example methanolic hydrochloric acid.

When $P_1$ is benzyl or 4-methoxybenzyl, the protecting group may be cleaved using sodium in liquid ammonia.

When P is $P_2$ which is a group R'—S—, and R'=R, then typically the compound of formula (II) is a dimer of the compound of formula (I) in which $R_3$ is hydrogen.

When P is $P_2$ which is a group R'—S—, and R'=R, $P_2$ is identical to $R_3$, and so compounds of formula (II) in which $R_1^1$ is $R_1$, $R_2^1$ is $R_2$ and P is R—S— are themselves compounds of the invention.

When P is $P_2$ and R' is other than R, or $R_3$ in compounds of formula (I) is hydrogen, the disulphide bond may be cleaved by treatment with zinc and hydrochloric acid, sodium borohydride, an excess of a thiol such as β-mercaptoethanol or dithiothreitol, or by passing hydrogen sulphide through a solution of the disulphide.

Other conventional methods for removing sulphur protecting groups or cleaving disulphide bonds may also be used.

Where necessary, conversion of variables $R_1^1$ and $R_2^1$ to $R_1$ and $R_2$ respectively may be carried out using procedures commonly used in the organic chemistry of aromatic compounds. Unless they are unstable under the reaction conditions used to prepare the compounds of the invention, variables $R_1^1$ and $R_2^1$ in compounds of formula (II) are generally identical to variables $R_1$ and $R_2$ respectively in compounds of formula (I).

The intermediate compounds of formula (II) may be prepared by treating a compound of formula (III):

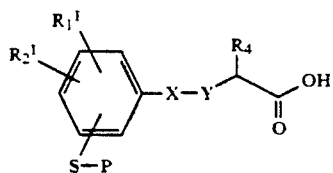

(III)

in which $R_1^1$, $R_2^1$, $R_4$, X, Y and P are as defined in formula (II), with a compound of formula (IV):

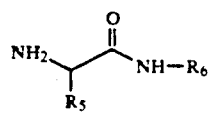

(IV)

in which $R_5$ and $R_6$ are as defined in formula (I).

The reaction is preferably carried out in the presence of a coupling agent such as N,N'-dicyclohexylcarbodiimide or N-ethyl-N'-dimethylaminopropylcarbodiimide.

Compounds of formula (II) in which P is $P_2$, which is a group R'—S— where R'=R, which compounds are compounds of the invention of formula (I), may be prepared by oxidative coupling, with iodine or oxygen, of compounds of formula (I) in which $R_3$ is hydrogen.

The intermediate compounds of formula (III) may be prepared by hydrolysis and subsequent decarboxylation of malonic ester derivatives of formula (V):

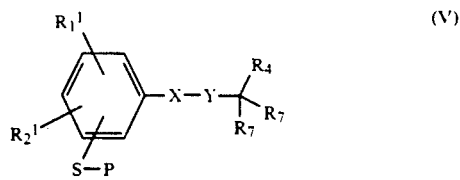

(V)

in which $R_1^1$, $R_2^1$, $R_4$, X, Y and P are as defined in formula (II) and each $R_7$ is a hydrolysable ester group.

The hydrolysis may be carried out under basic conditions, for example by heating in aqueous sodium or potassium hydroxide solution.

Decarboxylation of the resulting malonic acid derivative may be carried out by heating in a high boiling solvent, for example xylene.

The intermediate compounds of formula (V) may be prepared by reaction of a compound of formula (VI):

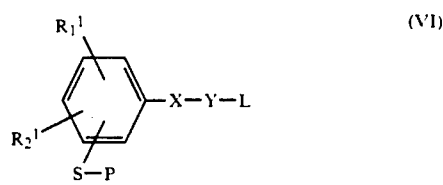

(VI)

in which $R_1^1$, $R_2^1$, X, Y and P are as defined in formula (II) and L is a leaving group, with a compound of formula (VII):

(VII)

in which $R_4$ and $R_7$ are as defined in formula (V).

The reaction is preferably carried out by a standard malonic ester synthesis in which the ester groups $R_7$ in the compound of formula (VII) are ethyl ester groups.

Suitable values for the leaving group L in compounds of formula (VI) include halogen such as chlorine and bromine, and sulphonyloxy derivatives such as methanesulphonyloxy and p-toluenesulphonyloxy.

The leaving group L in compounds of formula (VI) may be introduced using standard procedures. For example, a halogen leaving group L may be introduced by reaction of a compound of formula (VI) in which L is an amino function with, for example, ethyl chloroformate, whilst a sulphonyloxy leaving group may be introduced by reaction of a compound of formula (VI) in which L is hydroxy with, for example, a sulphonyl halide such as methanesulphonyl chloride or p-toluenesulphonyl chloride, suitably at reduced temperature and in the presence of a chloride-ion scavenger.

At ambient temperature and in the absence of a scavenger, the sulphonyloxy group so introduced may be readily displaced by chloride ions to provide a chlorine leaving group.

Alternatively, the intermediate compounds of formula (III) may be prepared directly by reaction of compounds of formula (VI) with the dianion of compounds of formula (VII) in which one $R_7$ is hydrogen and the other $R_7$ is a carboxyl group. This procedure necessitates the use of a sulphur protecting group $P_1$ in compounds of formula (VI) which has no acidic protons, for example a tertiary butyl group.

The compounds of formula (IV) are either known amino acid derivatives or can be made from these derivatives by known methods.

Malonic ester compounds of formula (VII) are generally known compounds or can be prepared using standard procedures from known compounds.

The intermediate compounds of formulae (III), (V) and (VI) disclosed herein are in some forms novel compounds and form an aspect of the present invention as do the described processes for their preparation.

Compounds of formula (VI) in which n is 0 may be prepared by according to methods described by C. P. Klein and C. R. Hauser, J.Org. Chem., 32, 1479, (1967) and H. W. Gschwend and H. R. Rodriguez, Org. Reactions, 26, 83, (1979), by introduction of the thio moiety P-S-to a benzylamine derivative, suitably an N,N-dimethyl benzylamine derivative. For example, where P is $P_1$ which is an optionally substituted benzyl group, the benzylamine derivative may be treated with n-butyl lithium and the appropriate benzyl disulphide at reduced temperature in an inert solvent. Conversion of the amino function to a suitable leaving group L may be carried out as hereinbefore described.

Compounds of formula (VI) in which n is 1 may be prepared from the appropriate thiobenzaldehyde by reaction with the Wittig reagent (methoxymethyl)triphenylphosphonium chloride and subsequent hydrolysis of the resulting enol ether to give the corresponding phenyl acetaldehyde, according to the method of G. Wittig et al., Chem. Ber., 95, 2514, (1962). The reaction may be repeated to give the corresponding n = b 2 compound. The aldehyde group may be reduced to —CH$_2$OH with sodium borohydride, and the alcohol further converted to the desired leaving group L.

Compounds of formula (VI) in which P is $P_2$ which is a group R'—S— may be prepared by oxidative coupling of the appropriate phenyl mercaptan with a compound R'—SH.

Similarly, compounds of formula (VI) in which P is $P_1$ where $P_1$ is an acyl group may be prepared by acylation of the corresponding phenylmercaptan.

Where obtainable, pharmaceutically acceptable salts of the compounds of formula (I) may be formed conventionally by reaction with the appropriate acid or base. Solvates may be formed by crystallization from the appropriate solvent.

As mentioned previously, the compounds of formula (I) exist in more than one diastereoisomeric form. Where the processes of the invention produce mixtures thereof, the individual isomers may be separated one from another by chromatography, e.g. by HPLC or by conventional silica gel column chromatography.

Alternatively, separate diastereoisomeric compounds of formula (I) can be obtained by using stereoisomerically pure starting materials or by separating desired isomers of intermediates at any stage in the overall synthetic process, and converting these intermediates to compounds of formula (I).

The present invention further provides a pharmaceutical composition, which comprises a compound of formula (I), or a pharmaceutically acceptable salt, solvate or hydrate thereof, and a pharmaceutically acceptable carrier.

A composition of this invention is useful in the treatment of rheumatism and arthritis and in the treatment of other collagenolytic conditions.

A composition of the invention, which may be prepared by admixture, may contain a diluent, binder, filler, disintegrant, flavouring agent, colouring agent, lubricant or preservative in conventional manner. These conventional excipients may be employed in conventional manner, for example as in the preparation of compositions of related peptide enzyme inhibitors, such as the ACE inhibitor captopril.

A composition of the invention may be adapted for oral, topical, percutaneous, rectal or parenteral—intravenous, intramuscular, sub-cutaneous, intradermal or intra-articular administration, but oral administration is preferred.

Preferably, a pharmaceutical composition of the invention is in unit dosage form and in a form adapted for use in the medical or veterinarial fields. For example, such preparations may be in a pack form accompanied by written or printed instructions for use as an agent in the treatment or prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen.

The compound or composition of the invention may be formulated for administration by any route, the preferred route depending upon the disorder for which treatment is required, and is preferably in unit dosage form or in a form that a human patient may administer to himself in a single dosage.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients. For example, in a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository or for parenteral administration in an injectable form. For injection, for example by intra-articular injection as poorly dispersed depot stores, the compounds of the invention may be presented in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers or solutes to render the solution isotonic with the blood, thickening agents, suspending agents or other pharmaceutically acceptable additives. Such forms will be presented in sterile unit dose form such as ampoules or disposable injection devices or in multi- dose forms such as a bottle from which the appropriate dose may be withdrawn or a solid form or concentrate which can be used to prepare an injectable formulation.

For topical and percutaneous administration, the preparations may also be presented as an ointment, cream, lotion, gel, spray, aerosol, wash or skin paint or patch.

A unit dose for inflammatory diseases will generally contain from 10 to 1000 mg and preferably will contain from 10 to 500 mg, in particular 10, 50, 100, 150, 200, 250, 300, 350, 400, 450 or 500 mg. The composition may be administered once or more times a day, for example 2, 3 or 4 times daily, so that the total daily dose for a 70 kg adult with normally be in the range 10 to 3000 mg. Alternatively, in particular for injection, the unit dose will contain from 2 to 200 mg of a compound of the invention and be administered in multiples, if desired, to give the desired daily dose.

The present invention additionally provides a method of treating a collagenolytic condition such as rheumatism and/or arthritic conditions, or cancer, or other diseases in which enzyme-mediated breakdown of connective tissue components plays a role in mammals, such as humans, which comprises administering an effective amount of a compound of formula (I) or a pharmaceutically acceptable salt, solvate or hydrate thereof, to the mammal.

The present invention also provides the use of a compound of formula (I) or a pharmaceutically acceptable salt, solvate or hydrate thereof, for the manufacture of a medicament for use as an active therapeutic substance, particularly in the treatment of collagenolytic conditions, such as rheumatism, cancer, bone disorders, skin diseases, periodontal disease or corneal ulceration, in mammals.

The following Descriptions and Examples illustrate the preparation of compounds of the invention and the subsequent biological data illustrates their pharmacological activity. All temperatures are expressed in °C.

DESCRIPTION 1

2-(2-Benzylthiobenzyl)-2-(2-methylpropyl)malonic acid, diethyl ester (D1)

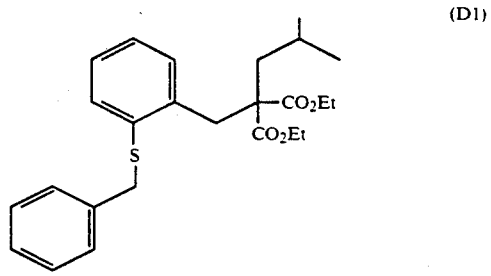

Sodium hydride (0.49 g of an 80% suspension, 16.3 mmol) was washed with dry toluene, then was suspended in dry DMF (30 ml). Diethyl isobutylmalonate (3.1 g, 15 mmol) was added dropwise and the mixture was stirred for 60 min. 2-Benzylthiobenzyl chloride[1] (3.68 g, 14.8 mmol) was added in two portions, and after 20 min, the mixture was heated at 100° C. for 3 h. The solvent was evaporated in vacuo and the residue was partitioned between water and ether. The ethereal layer was washed with water and brine then was dried ($MgSO_4$) and evaporated. Column chromatography (150 g $SiO_2$) of the residue, eluting with 10–20% ether/pentane gave the title compound (3.43 g, 54%) as an oil.

δ ($CDCl_3$): 0.83 (6H,d,J=Hz), 1.17 (6H,t,J=7 Hz), 1.7–1.85 (3H,m), 3.43 (2H,s), 4.0 (2H,s), 4.09 (4H, two q's, J=7 Hz) and 7.1–7.4 (9H, m).

Reference 1. G. W. Stacey, F. W. Villaescusa and T. E. Wollner, *J. Org. Chem.*, 1965, 30, 4074.

DESCRIPTION 2

2-Benzylthio-α-(2-methylpropyl)phenylpropanoic acid (D2)

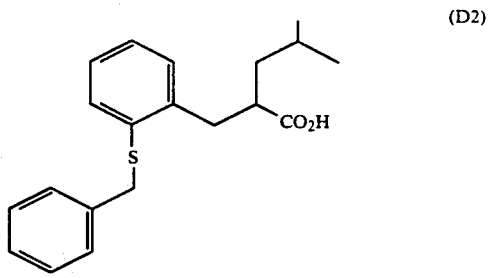

2-(2-Benzylthiobenzyl)-2-(2-methylpropyl)malonic acid, diethyl ester (3 g, 7 mmol) was added to a solution of 85% potassium hydroxide (1.38 g, 21 mmol) in water (1 ml) and ethanol (3 ml). The mixture was heated under reflux for 3 h, then was cooled, diluted with water, acidified with 5M hydrochloric acid and extracted with ethyl acetate. The extracts were washed with water and brine, then dried ($MgSO_4$) and evaporated in vacuo. The residual oil was heated under reflux in dry xylene (40 ml) for 6 h. The solvent was evaporated, the residue was dissolved in ether and was extracted with 5% sodium hydroxide (2×20 ml). The extracts were washed with ether, acidified with 2M hydrochloric acid, then were extracted with ether. The extracts were washed with water and brine, then dried (MgSO4) and evaporated to leave the title compounds as an oil (810 mg). The non-acidic material obtained from the xylene treatment was re-saponified to give a further batch of the title compound (390 mg). Total yield 1.17 g (51%).

δ (CDCl3) 0.88 (3H,d,J=7 Hz), 0.90 (3H,d,J=7 Hz), 1.28 (1H,m), 1.62 (2H,m), 2.88 (3H,m), 4.10 (2H,s) and 7.02–7.30 (9H,m).

DESCRIPTION 3

2-Benzylthio-N-2-(4-methoxyphenyl)-1-(S)-(methylaminocarbonyl)ethyl]-α-(2-methylpropyl)phenylpropanamide (D3)

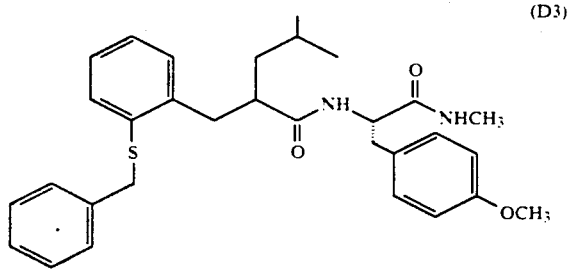

N,N'-Dicyclohexylcarbodiimide (0.83 g, 4.0 mmol) was added to an ice-cooled solution of 2-benzylthio-α-(2-ethylpropyl)phenylpropanoic acid (1.20 g, 3.65 mmol) in dry dichloromethane (30 ml). After 15 min, O-methyl-L-tyrosine N-methylamide (0.76 g, 3.65 mmol) was added and the mixture was stirred at room temperature overnight. The mixture was cooled in ice for 60 min, filtered, and the filtrate was washed successively with water, 1M hydrochloric acid water, saturated sodium hydrogen carbonate and brine. The solution was dried (MgSO4) and evaporated in vacuo to leave a foam. Column chromatography (50 g SiO2), eluting with 50% ethyl acetate/pentane gave:

Isomer A (faster running isomer), 178 mg, mp 143°–147° C. (Found: C,71.52; H,7.45; N,5.36. C31H38N2O3S requires C,71.78; H,7.38; N,5.40%).

δ (CDCl3) 0.84 (6H,t,J=7 Hz), 1.28 (2H,m), 1.4–1.65 (1H,m), 2.60 (3H,d,J=5 Hz), 2.45–2.80 (5H,m), 3.77 (3H,s), 4.13 (2H,m), 4.30 (1H,m), 5.47 (1H, brs), 5.63 (1H,brd), 6.73 (2H,d,J=8 Hz), 6.93 (2H,d,J=8 Hz) and 7.05–7.40 (9H,m).

and Isomer B (slower running isomer), 253 mg, mp 143°–145° C. (Found: C,71.65; H,7.41; N,5.33. C31H38N2O3S requires C,71.78; H,7.38; N,5.40%).

δ (CDCl3): 0.71 (3H,d,J=6 Hz), 0.76 (3H,d,J=6 Hz), 0.95–1.15 (2H,m), 1.45 (1H,m), 2.30 (1H,m), 2.50 (3H,d,J=6 Hz), 2.65–2.80 (3H,m), 3.07 (1H,dd,J=7,14 Hz), 3.77 (3H,s), 4.05 (1H,d,J=13 Hz), 4.17 (1H,d,J=13 Hz), 4.57 (1H,q,J=8 Hz), 5.0 (2H,m), 6.79 (2H,d,J=8 Hz) and 7.0–7.4 (11H,m).

DESCRIPTION 4

2-Benzylthio-3-methoxy-N,N-dimethyl benzylamine (D4)

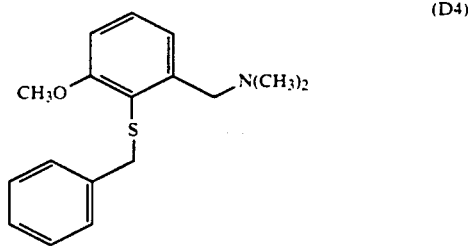

A 1.6M solution of n-butyl lithium in hexane (7.0 ml, 11.3 mmol) was added at room temperature to a solution of 3-methoxy-N,N-dimethyl benzylamine (1.55 g, 9.4 mmol) in dry ether (30 ml). The solution was kept under nitrogen for 18 h, then a solution of benzyl disulphide (2.78 g, 11.3 mmol) in dry tetrahydrofuran (10 ml) was added over 10 min. After 45 min, water was added. The ethereal layer was extracted with 2M hydrochloric acid (3×5 ml). The acidic solution was washed with ether and was made basic with 10% sodium hydroxide, and extracted with ether. The organics were washed with water and brine then were dried (K2CO3), evaporated and recrystallized from ethyl acetate/hexane to leave the title compound (1.65 g, 61%), mp 69°–70° C. (Found: C,70.75; H,7.07; N,4.84. C17H21NOS requires C,71.04; H,7.36; N,4.87%).

δ (CDCl3): 2.13 (6H,s), 3.40 (2H,s), 3.92 (3H,s), 3.97 (2H,s), 6.80 (1H,d,J=8 Hz), 7.00 (1H,d,J=8 Hz) and 7.03–7.28 (6H,m).

DESCRIPTION 5

2-Benzylthio-3-methoxybenzyl chloride (D5)

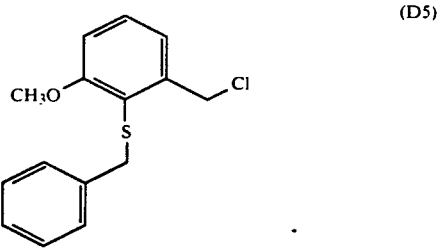

Ethyl chloroformate (0.6 ml, 6.2 mmol) was added dropwise to an ice-cooled solution of 2-benzylthio-3-methoxy-N,N-dimethyl benzylamine (1.5 g, 5.2 mmol) in dry ether (40 ml). The mixture was stirred at room temperature for 2 h. The solvent was evaporated in vacuo, and the residual solid was extracted several times with hexane. The extracts were evaporated to leave the title compound as a solid (1.29 g, 89%), mp 54°–55C. (Found: C,64.67; H,5.50; Cl,12.99. C15H15ClOS requires C,64.62; H,5.42; Cl,12.72%).

δ (CDCl3): 3.83 (3H,s), 3.92 (2H,s), 4.50 (2H,s), 6.8 (1H,dd,J=8,2 Hz) and 6.9–7.2 (7H,m).

DESCRIPTION 6

2-(2-Benzylthio-3-methoxybenzyl)-2-(2-methylpropyl)-malonic acid, diethyl ester (D6)

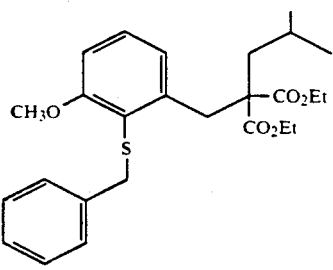
(D6)

Treatment of 2-benzylthio-3-methoxybenzyl chloride (1.11 g, 4 mmol) in a manner similar to that described in Description 1 gave the title compound as an oil (1.53 g, 84%).

δ (CDCl$_3$): 0.80 (6H,d,J=6 Hz), 1.17 (6H,t,J=7 Hz), 1.75 (3H,brs), 3.40 (2H,s), 3.88 (5H,s), 4.10 (4H,q,J=7 Hz), 6.76 (2H,brd,J=7 Hz) and 7.05-7.20 (6H,m).

DESCRIPTION 7

2-Benzylthio-3-methoxy-α-(2methylpropylphenyl-propanoic acid (D7)

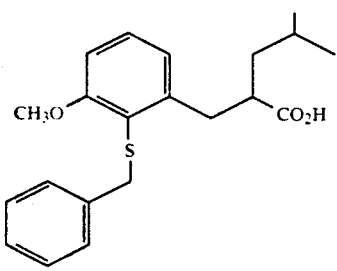
(D7)

Hydrolysis and decarboxylation of 2-(2-benzylthio-3-methoxybenzyl)-2-(2-methylpropyl)malonic acid, diethyl ester (1.5 g) in a manner similar to that described in Description 2 gave the title compound as an oil (750 mg, 64%).

δ (CDCl$_3$): 0.85 (6H,t,J=5 Hz), 1.23 (1H,m), 1.55 (2H,m), 2.7-2.95 (3H,m), 3.92 (3H,s), 3.97 (2H,d,J=7 Hz), 6.76 (2H,m) and 7.1-7.25 (6H,m).

DESCRIPTION 8

2-Benzylthio-3-methoxy-N-[2-(4-methoxyphenyl)-1-(S)-(methylaminocarbonyl)ethyl]-α-(2-methylpropyl)-phenylpropanamide (D8)

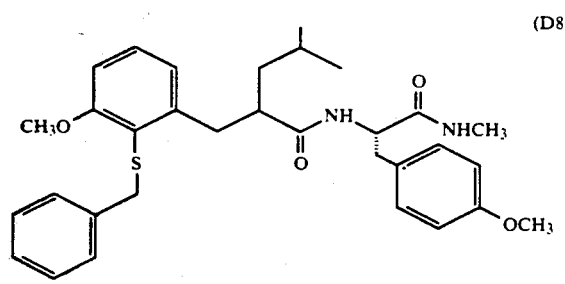
(D8)

N-Ethyl-N'-dimethylaminopropylcarbodiimide (420 mg, 2.2 mmol) was added to an ice-cooled solution of 2-benzylthio-3-methoxy-α-(2-methylpropyl)phenyl-propanoic acid (750 mg, 2.1 mmol) in dichloromethane (30 ml). After 10 min, O-methyl-L-tyrosine N-methylamide (435 mg, 2.1 mmol) was added and the mixture was stirred at room temperature overnight. The mixture was diluted was dichloromethane and was washed successively with water, saturated sodium hydrogen carbonate, water, 1M hydrochloric acid and brine, then was dried (MgSO$_4$) and evaporated in vacuo. Column chromatography of the residue (50 g SiO$_2$), eluting with 50% ethyl acetate/pentane gave: Isomer A (faster running isomer), 163 mg, mp 134°-136° C. (ethyl acetate/hexane).

δ (CDCl$_3$): 0.72 (3H,d,J=7 Hz), 0.76 (3H,d,J=7 Hz), 1.1-1.5 (3H,m), 2.08 (1H,m), 2.46-2.64 (3H,m), 2.58 (3H,d,J=4 Hz), 2.73 (1H,dd,J=13,6 Hz), 3.70 (3H,s), 3.86 (1H,d,J=12 Hz), 3.88 (3H,s), 4.06 (1H,d,J=12 Hz), 4.25 (1H,q,J=7 Hz), 5.30 (1Hd,J=7 Hz), 5.55 (1H,m) and 6.6-7.2 (12H,m).

Isomer B (slower running isomer), 212 mg, mp 158°-161° C. (ethyl acetate/hexane).

(Found: C,70.04; H,7.28; N,5.07. C$_{32}$H$_{40}$H$_2$O$_4$S requires: C,70.04; N,7.35; N,5.11%).

δ (CDCl$_3$): 0.68 (3H,d,J=7 Hz), 0.73 (3H,d,J=7 Hz), 0.8-1.45 (3H;m), 1.97 (1H,m), 2.55 (3H,d,J=4 Hz), 2.5-2.8 (3H,m), 3.15 (1H, dd,J=13,5 Hz), 3.76 (3H,s), 3.85 (1H,d,J=13 Hz), 3.97 (3H,s), 4.32 (1H,d,J=13 Hz), 4.55-4.7 (2H,m), 5.08 (1H,m) and 6.65-72 (12H,m).

DESCRIPTION 9

3-Trifluoromethyl-2-(4-methoxybenzylthio)-N,N-dimethyl benzylamine (D9)

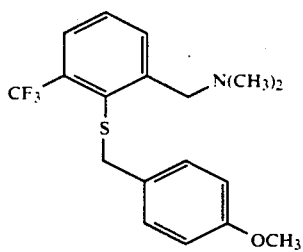
(D9)

A 1.6M solution of n-butyl lithium in hexane (6.6 ml, 10.5 mmol) was added slowly to a cooled solution of 3-trifluoromethyl-N,N-dimethylbenzylamine (2.03 g, 10 mmol) n dry ether (25 ml). After 2h, a solution of 4-methoxybenzyldisulphide (3.06 g, 10 mmol) in dry THF (25 ml) was added over 10 min to the dark reaction mixture. After 30 min, water was added and the aqueous layer was extracted with ether. The combined organics were extracted with 2N hydrochloric acid (3×10 ml). The acidic solution was washed with ether then was made basic with 10% sodium hydroxide and was extracted with ether. The extracts were washed with water and brine, then were dried (K$_2$CO$_3$) and evaporated to leave an oil. Column chromatography on silica gel (100 g), eluting with ethyl acetate gave the title compound as an oil (1.74 g, 49%).

δ (CDCl$_3$): 2.23 (6H,s), 3.60 (2H,s), 3.78 (3H,s), 3.92 (2H,s), 6.78 (2H,d,J=8 Hz), 7.12 (2H,d,J=8 Hz), 7.43 (1H,t,J=8 Hz), 7.66 (1H,d,J=8 Hz) and 7.71 (1H,D,J=8 Hz).

DESCRIPTION 10

3-Trifluoromethyl-2-(4-methoxybenzylthio)benzyl chloride (D10)

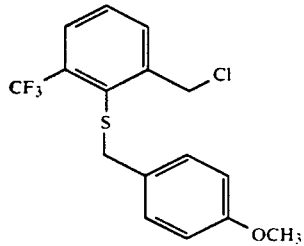

The title compound, prepared from 3-trifluoromethyl-2-(4-methoxybenzylthio)-N,N-dimethylbenzylamine (D9) (1.75 g, 4.9 mmol) in a manner similar to that described in Description 5, was obtained as an oil (1.24 g, 73%).

Found: C,55.10; H,4.08. $C_{16}H_{14}ClF_3OS$ requires C,55.41; H,4.07%.

δ (CDCl$_3$): 3.78 (3H,s), 3.97 (2H,s), 4.73 (2H,s), 6.80 (2H,d,J=8 Hz), 7.08 (2H,d,J=8 Hz), 7.49 (1H,t,J=8 Hz) and 7.72 (2H,m).

DESCRIPTION 11

2-(3-Trifluoromethyl-2-(4-methoxybenzylthio)benzyl)-2-(2-methylpropyl)malonic acid, diethyl ester (D11)

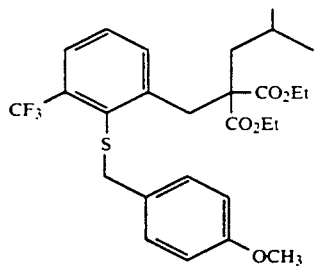

Treatment of 3-trifluoromethyl-2-(4-methoxybenzylthio)benzyl chloride (D10) (1.07 g, 3 mmol) in a manner similar to that described in Description 1 gave the title compound as an oil (1.22 g, 78%).

δ (CDCD$_3$): 0.83 (6H,d,J=7 Hz), 1.13 (6H,t,J=7 Hz), 1.70 (1H,m), 1.79 (2H,d,J=6 Hz), 3.48 (2H,s), 3.77 (3H,s), 3.78 (2H,s), 4.04 (4H,m), 6.77 (2H,d,J=9 Hz), 7.04 (2H,d,J=9 Hz), 7.34 (1H,d,J=8 Hz), 7.51 (1H,d,J=8 Hz) and 7.63 (1H,d,J=8 Hz).

DESCRIPTION 12

3-Trifluoromethyl-2-(4-methoxybenzylthio)-α-(2-methylpropyl)phenylpropanoic acid (D12)

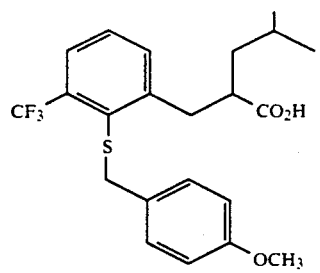

A solution of 2-(3-trifluoromethyl-2-(4-methoxybenzylthiol)benzyl)-2-(2-methylpropyl)malonic acid, diethyl ester (D11) (1.18 g, 2.24 mmol) in ethanol (3 ml) and 40% sodium hydroxide solution (3 ml) was heated under reflux for 16 h. The cooled solution was diluted with water, acidified with 2N hydrochloric acid and was extracted with ethyl acetate. The extracts were washed with water and brine, then were dried (MgSO$_4$) and evaporated in vacuo. The residual oil was dissolved in dry xylene (50 ml) and heated under reflux for 3.5 h. The solvent was evaporated to leave the title compound as an oil (790 mg, 83%).

δ(CDCl$_3$): 0.88 (6H,d,J=7 Hz), 1.25 (1H,m), 1.61 (2H,m), 2.75-3.0 (3H,m), 3.78 (3H,s), 3.83 (1H,d,J=11 Hz), 3.90 (1H,d,J=11 Hz), 6.78 (2H,d,J=9 Hz), 7.07 (2H,d,J=9 Hz), 7.1-7.42 (2H,m) and 7.65 (1H,d,J=8 Hz).

DESCRIPTION 13

3-Trifluoromethyl-2-(4-methoxybenzylthio)-N-[2-(4-methoxyphenyl)-1-(S)-methylaminocarbonyl)ethyl]-α-(2-methylpropyl)phenylpropanamide (D13)

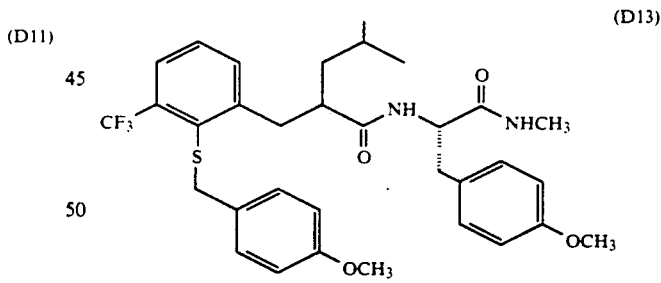

Treatment of 3-trifluoromethyl-2-(4-methoxybenzylthio)-α-(2-methylpropyl)phenylpropanoic acid (D12) (770 mg, 1.8 mmol) in a manner similar to that described in Description D8 gave the title compound as a 1:1 mixture of two diastereoisomers (500 mg, 45%) mp 93°-105° C.

δ (CDCl$_3$): 0.72 (3H,d,J=6 Hz), 0.78 (3H,d,J=6 Hz), 0.85 (6H,d,J=6 Hz), 1.05-1.3 (4H,m), 1.4-1.6 (2H,m), 2.3-2.5 (3H,m), 2.58 (3H,d,J=5 Hz), 2.62 (3H,d,J=5 Hz), 2.7-2.9 (6H,m), 2.95 (1H,dd,J=6,13 Hz), 3.76 (3H,x), 3.78 (3H,s), 3.85 (4H,m), 4.36 (1H,m), 4.46 (1H,q,J=5 Hz), 5.43 (2H,brm), 5.65 (1H,d,J=7 Hz), 5.84 (1H,d,J=7 Hz), 6.72-6.88 (10H,m), 7.05 (6H,d,J=9 Hz), 7.28-7.43 (4H,m), and 7.63 (2H,m).

DESCRIPTION 14

4-Methoxy-2-(4-methoxybenzylthio)-N,N-dimethylbenzylamine (D14)

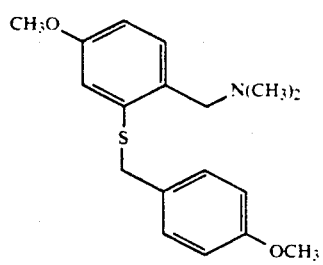
(D14)

A 1.6M solution of n-butyl lithium in hexane (2.7 ml, 4 mmol) was added at room temperature to a solution of 4-methoxy-N,N-dimethylbenzylamine (0.67 g, 4 mmol) in dry ether (30 ml). The solution was kept under nitrogen for 18 h, then a solution of 4-methoxybenzyl disulphide (1.25 g, 4 mmol) in dry ether (50 ml) was added over 2 min. After 10 min water was added. The ethereal layer was extracted with 2N hydrochloric acid (2×10 ml). The acidic solution was washed with ether, then was made basic with 10% sodium hydroxide, and was extracted with ether. The organics were washed with water and brine, then were dried (K$_2$CO$_3$) and evaporated to leave an oil. Column chromatography on silica gel (30 g), eluting with ethyl acetate gave the title compound as an oil (583 mg, 46%).

δ (CDCl$_3$): 2.25 (6H,s), 3.43 (2H,s), 3.78 (3H,s), 3.83 (3H,s), 4.0 (2H,s), 6.27 (1H,dd,J=8.2 Hz), 6.86 (2H,d,J=8 Hz), 6.90 (1H,d,J=2 Hz), 7.23 (1H,d,J=8 Hz) and 7.28 (2H,d,J=8 Hz).

DESCRIPTION 15

4-Methoxy-2-(4-methoxybenzylthio)benzyl chloride (D15)

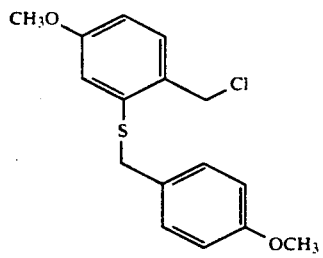
(D15)

The title compound, prepared from 4-methoxy-2-(4-methoxybenzylthio)-N,N-dimethylbenzylamine (D14) in a manner analogous to that described in Description 5, was obtained as an oil.

δ (CDCl$_3$): 3.68 (3H,s), 3.74 (3H,s), 4.03 (2H,s), 4.64 (2H,s), 6.5–6.8 (3H,m) and 7.–7.4 (4H,m).

DESCRIPTION 16

2-(4-Methoxy-2-(4-methoxybenzylthio)benzyl)-2-(2-methylpropyl)malonic acid, diethyl ester (D16)

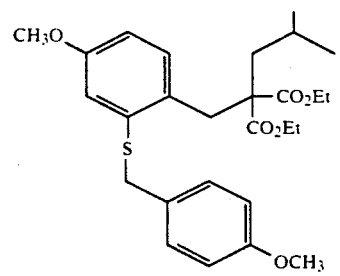
(D16)

Treatment of 4-methoxy-2-(4-methoxybenzylthio)benzyl chloride (D15) (2.19 g, 7.1 mmol) in a manner similar to that described in Description 1 gave the title compound as an oil (1.38 g, 40%) which crystallised slowly on standing, mp 59°-60.5° C.

δ (CDCl$_3$) : 0.84 (6H,d,J=7 Hz), 1.18 (6H,t,J=7 Hz), 1.57 (1H,s), 1.80 (2H,m), 3.38 (2H,s), 3.71 (3H,s), 3.77 (3H,s), 3.97 (2H,s), 4.12 (4H,m), 6.65 (1H,dd,J=8.3 Hz), 6.80 (2H,d,J=9 Hz), 6.83 (1H,d,J=3 Hz), 7.17 (1H,d,J=8 Hz) and 7.16 (2H,d,J=9 Hz).

DESCRIPTION 17

4-Methoxy-2-(4-methoxybenzylthio)-α-(2-methylpropyl)phenylpropanoic acid (D17)

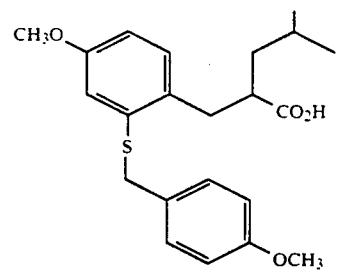
(D17)

Hydrolysis and decarboxylation of 2-(4-methoxy-2-(4-methoxybenzylthio)benzyl)-2-(2-methylpropyl)malonic acid, diethyl ester (D16) (1.35 g, 2.8 mmol) in a manner similar to that described in Description 12 gave the title compound as an oil (1.04 g, 96%).

δ (CDCl$_3$): 0.87 (6H,t,J=7 Hz), 1.25 (1H,m), 1.60 (2H,m), 2.82 (3H,m), 3.70 (3H,s), 3.80 (3H,s), 4.05 (2H,s), 6.62 (1H,dd,J=8.2 Hz), 6.80 (1H,d,J=2 Hz), 6.82 (2H,d,J=8 Hz), 7.04 (1H,d,J=8 Hz) and 7.20 (2H,d,J=8 Hz).

DESCRIPTION 18

4-Methoxy-2-(4-methoxybenzylthio)-N-[2-(4-methoxyphenyl)-1-(S)-(methylaminocarbonyl)ethyl]-α-(2-methylpropyl)phenylpropanamide (D18)

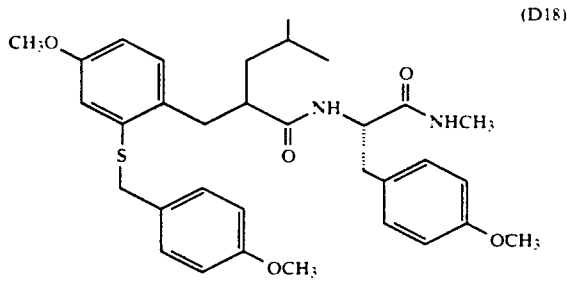

Treatment of 4-methoxy-2-(4-methoxybenzylthio)-α-(2-methylpropyl)phenylpropanoic acid (D17) (460 mg, 1.2 mmol) in a manner similar to that described in Description 8 gave the title compound as a 1:1 mixture of two diastereoisomers (330 mg, 48%), mp 150°–158° C.

Found: C,68.32; H,7.02; N,4.84%. $C_{33}H_{42}N_2O_2S$ requires C,68.48; H,7.31; N,4.84%.

δ (CDCl$_3$): 0.70 (3H,d,J=6 Hz), 0.75 (3H,d,J=6 Hz), 0.83 (6H,t,J=6 Hz), 1.05–1.70 (6H,m), 2.3–2.8 (9H,m), 2.51 (3H,d,J=4 Hz), 2.63 (3H,d,J=4 Hz), 3.13 (1H,dd,J=5,14 Hz), 3.72 (3H,s), 3.75 (3H,s), 3.78 (12H,4xs), 4.02 (1H,d,J=15 Hz), 4.08 (2H,s), 4.13 (1H,d,J=15 Hz), 4.37 (1H,m), 4.59 (1H,m), 5.0 (2H,brm), 5.58 (1H,brm), 5.75 (1H,d,J=7 Hz), 6.60 (2H,m), 6.75–7.04 (16H,m) and 7.23 (4H,m).

DESCRIPTION 19

4-Chloro-2-(4-methoxybenzylthio)-N,N-dimethylbenzylamine (D19)

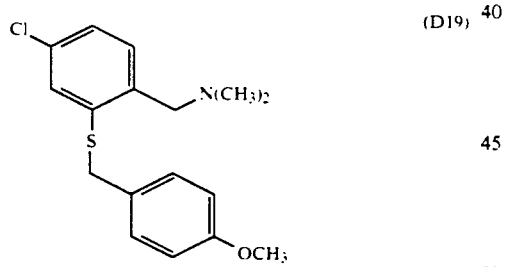

A 1.2M solution of n-butyl lithium in hexane (7.7 ml, 9.2 mmol) was added to an ice-cooled solution of 4-chloro-N,N-dimethylbenzylamine (1.57 g, 9.3 mmol) in dry ether (50 ml). The solution was allowed to warm slowly to room temperature, and after 2.5 h it was added, over 15 min, to an ice-cooled solution of 4-methoxybenzyl disulphide (2.84 g, 9.3 mmol) in dry THF (40 ml). After 1.5 h water was added and the organic layer was extracted with 2N hydrochloric acid (3×15 ml). The acidic solution was washed with ether then was made basic with 10% sodium hydroxide, and was extracted with ether. The extracts were washed with water and brine, then were dried (K$_2$CO$_3$) and evaporated to leave a pale green oil. Column chromatography on silica gel (75 g), eluting with ethyl acetate gave the title compound as a solid (1.81 g, 61%), mp 66°–68° C. (ethyl acetate/pentane).

Found: C,63.31; H,6.09; N,4.28%. $C_{17}H_{20}ClNOS$ requires C,63.44; H,6.26; N,4.35%.

δ (CDCl$_3$): 2.20 (6H,s), 3.38 (2H,s), 3.80 (3H,s), 4.07 (2H,s), 6.83 (2H,d,J=9 Hz), 7.10 (1H,dd,J=9,2 Hz), 7.23 (3H,d,J=9 Hz) and 7.28 (1H,d,J=2 Hz).

DESCRIPTION 20

4-Chloro-2-(4-methoxybenzylthio)benzyl chloride (D20)

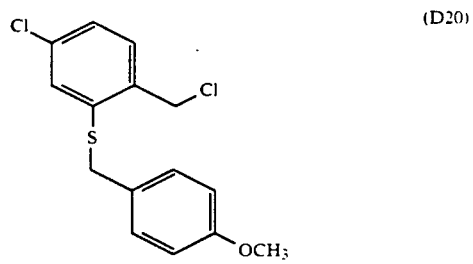

A solution of 4-chloro-2-(4-methoxybenzylthio)-N,N-dimethylbenzylamine (D19) (2.49 g, 7.7 mmol) in dry toluene (80 ml) was cooled in ice whilst ethyl chloroformate (0.9 ml, 9.4 mmol) was added dropwise. A solid slowly separated, and after 1 h at 0–5° C. the mixture was heated under reflux for 2 h. The solvent was removed in vacuo, then the residue was repeatedly dissolved in toluene and evaporated to dryness (3 times) to give the title compound as a light brown oil (2.36 g, 98%).

δ (CDCl$_3$): 3.79 (3H,s), 4.10 (2H,s), 4.62 (2H,s), 6.83 (2H,d,J=9 Hz), 7.18 (3H,m), 7.32 (1H,d,J=8 Hz) and 7.34 (1H,s).

DESCRIPTION 21

2-(4-Chloro-2-(4-methoxybenzylthio)benzyl)-2-(2-methylpropyl)malonic acid, diethyl ester (D21)

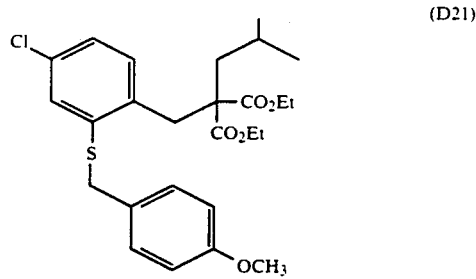

Treatment of 4-chloro-2-(4-methoxybenzylthio)benzyl chloride (D20) (3.22 g, 10.6 mmol) in a manner similar to that described in Description 1 gave the title compound as an oil (4.27 g, 82%) which crystallised slowly on standing, mp 95°–97° C.

δ (CDCl$_3$): 0.83 (6H,d,J=6 Hz), 1.16 (6H,t,J=7 Hz), 1.7–1.85 (3H,m), 3.36 (2H,s), 3.80 (3H,s), 3.99 (2H,s), 4.10 (4H,m), 6.81 (2H,d,J=8 Hz), 7.03–7.11 (2H,m), 7.15 (2H,d,J=8 Hz) ad 7.29 (1H,d,J=2 Hz).

DESCRIPTION 22

4-Chloro-2-(4-methoxybenzylthio)-α-(2-methylpropyl)-phenylpropanoic acid (D22)

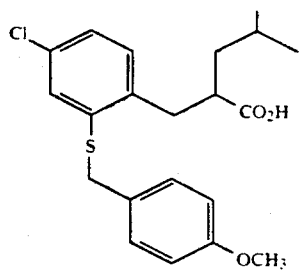

(D22)

Hydrolysis and decarboxylation of 2-(4-chloro-2-(4-methoxybenzylthio)benzyl)-2-(2-methylpropyl)malonic acid, diethyl ester (D21) (2.61 g, 5.3 mmol) in a manner similar to that described in Description 12 gave the title compound as an oil (2.03 g, 97%).

δ (CDCl$_3$): 0.87 (6H,t,J=7 Hz), 1.25 (1H,m), 1.60 (2H,m), 2.80 (3H,m), 3.80 (3H,s), 4.05 (2H,s), 6.85 (2H,d,J=8 Hz), 7.05 (2H,d,J=2 Hz), 7.23 (2H,d,J=8 Hz) and 7.26 (1H,d,J=2 Hz).

DESCRIPTION 23

4-Chloro-2-(4-methoxybenzylthio)-N-[2-(4-methoxyphenyl)-1-(S)-(methylaminocarbonyl)ethyl]-α-(2-methylpropyl)phenylpropanamide (D23)

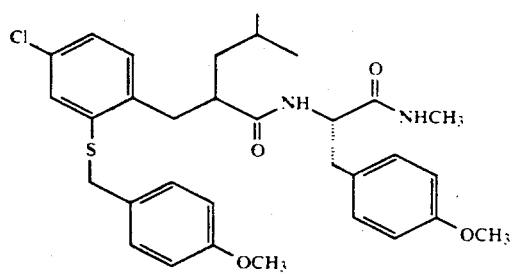

(D23)

Treatment of 4-chloro-2-(4-methoxybenzylthio)-α-(2-methylpropyl)phenylpropanoic acid (D22) (500 mg, 1.3 mmol) in a manner similar to that described in Description 8 gave the title compound as a 1:1 mixture of diastereoisomers (480 mg, 65%), mp 101°-166° C.

Found: C,65.91; H,6.88; N,4.71%. C$_{32}$H$_{39}$ClN$_2$O$_4$S requires: C,65.90; H,6.74; N,4.80%.

δ (CDCl$_3$): 0.64 (3H,d,J=5 Hz), 0.68 (3H,d,J=5 Hz), 0.76 (6H,t,J=5 Hz), 0.85-1.50 (6H,m), 2.25 (1H,m), 2.40 (1H,m), 2.50 (3H,d,J=4 Hz), 2.58 (3H,d,J=4 Hz), 2.4-2.7 (7H,m), 3.0 (1H,dd,J=6,14 Hz), 3.69 (6H,2xs), 3.73 (6H,2xs), 4.0 (4H,m), 4.27 (1H,m), 4.47 (1H,m), 4.96 (1H,brm), 5.05 (1H,d,J=8 Hz), 5.40 (1H,brm), 5.74 (1H,d,J=8 Hz), 6.68-6.80 (8H,m), 6.83-7.0 (8H,m) and 7.10-7.25 (6H,m).

DESCRIPTION 24

2-Chloro-6-(4-methoxybenzylthio)-N,N-dimethylbenzylamine (D24)

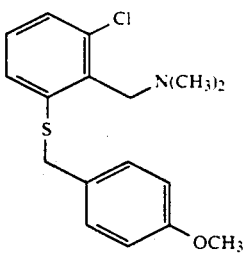

(D24)

Treatment of 2-chloro-N,N-dimethylbenzylamine using an analogous procedure to that described in Description 19 gave the title compound as a pale yellow solid (65%) mp 101°-104° C. (ethyl acetate/pentane).

Found: C,63.41; H,6.35; N,4.45%. C$_{17}$H$_{20}$ClNOS requires C,63.44; H,6.26; N,4.35%.

δ (CDCl$_3$): 2.28 (6H,s), 3.65 (2H,s), 3.80 (3H,s), 4.10 (2H,s), 6.83 (2H,d,J=8 Hz), 7.05-7.20 (3H,m) and 7.24 (2H,d,J=8 Hz).

DESCRIPTION 25

2-Chloro-6-(4-methoxybenzylthio chloride (D25)

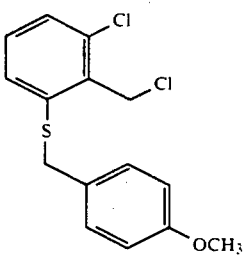

(D25)

2-Chloro-6-(4-methoxybenzylthio)-N,N-dimethylbenzylamine (D24) was treated in a manner analogous to that described in Description 20 to give the title compound as a solid (99%), mp 114°-119° C.

δ (CDCl$_3$): 3.78 (3H,s), 4.10 (2H,s), 4.90 (2H,s), 6.75 (2H,d,J=9 Hz) and 7.0-7.4 (5H,m).

DESCRIPTION 26

2-(2-Chloro-6-(4-methoxybenzylthio1benzyl)-2-(2-methylpropyl)malonic acid, diethyl ester (D26)

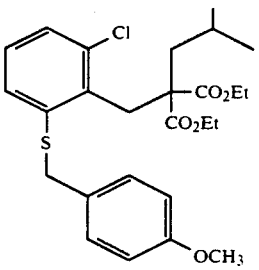

(D26)

Treatment of 2-chloro-6-(4-methoxybenzylthio)benzyl chloride (D25) (2.86 g, 9.15 mmol) in a manner similar to that described in Description 1, but with a reaction time of 16 h at 80° C., gave the title compound as a solid (3.03 g, 67%), mp 65°–74° C. (ethanol).

δ (CDCl₃): 0.83 (6H,d,J=6 Hz), 1.14 (6H,t,J=9 Hz), 1.75 (1H,m), 1.93 (2H,d,J=5 Hz), 3.71 (2H,s), 3.79 (3H,s), 3.99 (2H,s), 4.02 (4H,m), 6.80 (2H,d,J=9 Hz), 7.05 (1H,t,J=9 Hz), 7.14 (2H,d,J=9 Hz) and 7.16–7.26 (2H,m).

DESCRIPTION 27

2-Chloro-6-(4-methoxybenzylthio)-α-(2-methylpropyl)-phenylpropanoic acid (D27)

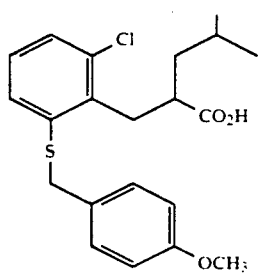

Hydrolysis and decarboxylation of 2-(2-chloro-6-(4-methoxybenzylthio)benzyl-2-(2-methylpropyl)malonic acid, diethyl ester (D26) (1.52 g, 3.1 mmol) in a manner similar to that described in Description 12 gave the title compound as an oil (1.19 g, 98%).

δ (CDCl₃): 0.81 (3H,d,J=7 Hz), 0.87 (3H,d,J=7 Hz), 1.17 (1H,m), 1.55 (1H,m), 1.78 (1H,m), 2.94 (1H,m), 3.07 (1H,dd,J=6,13 Hz), 3.25 (1H,dd,J=6,13 Hz), 3.79 (3H,s), 4.04 (2H,s), 6.82 (2H,d,J=9 Hz), 7.07 (1H,t,J=8 Hz) and 7.18 (4H,m).

DESCRIPTION 28

2-Chloro-6-(4-methoxybenzylthio)-N-[2-(4-methoxyphenyl-1-(S)-(methylaminocarbonyl)ethyl]-α-(2-methylpropyl)phenylpropanamide (D28)

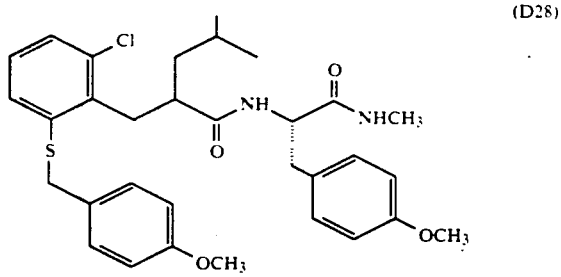

Treatment of 2-chloro-6-(4-methoxybenzylthio)-α-(2-methylpropyl)phenylpropanoic acid (D27) (990 mg, 2.5 mmol) in a manner similar to that described in Description 8 gave the title compound as a 1:1 mixture of two diastereoisomers (910 mg, 62%), mp 108°–128° C.

Found: C,66.17; H,66.5; N,4.72%. C₃₂H₃₉ClN₂O₄S requires C,65.90; H,6.74; N,4.80%.

δ (CDCl₃): 0.65 (3H,d,J=5 Hz), 0.77 (6H,d,J=5 Hz), 0.80 (3H,d,J=5 Hz), 1.0–1.80 (6H,m), 2.46–2.72 (3H,m), 2.62 (3H,d,J=4 Hz), 2.65 (3H,d,J=4 Hz), 2.75–3.03 (5H,m), 3.05–3.20 (2H,m), 3.76 (6H,s), 3.78 (6H,s), 4.05 (4H,m), 4.44 (1H,m), 4.55 (1H,q,J=7 Hz), 5.63 (2H,brm), 5.74 (1H,brm), 5.83 (1H,d,J=7 Hz), 6.73–6.75 (8H,m), 6 6.95–7.12 (6H,m) and 7.14–7.22 (8H,m).

DESCRIPTION 29

4-Chloro-2-(4-methoxybenzylthio)-N-[2-(3-indolyl)-1-(S)-methylaminocarbonyl)ethyl]-α-(2-methylpropyl)-phenylpropanamide (D29)

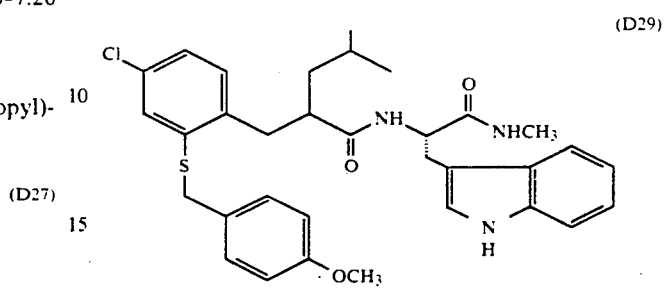

N-Ethyl-N'-dimethylaminopropylcarbodiimide (230 mg, 1.2 mmol) was added to an ice-cooled solution of 4-chloro-2-(4-methoxybenzylthio)-α-(2-methylpropyl)-phenylpropanoic acid (D22) (392 mg, 1 mmol) and 1-hydroxybenzotriazole (162 mg, 1.2 mmol) in dichloromethane (15 ml). After 15 min, O-methyl-L-tyrosine N-methylamide (218 mg, 1 mmol) was added. The mixture was stirred at room temperature for 48 h, then was diluted with dichloromethane, and was washed successively with water, 10% citric acid, water, saturated sodium hydrogen carbonate, and brine. The organic solution was dried (MgSO₄) and evaporated to leave a foam. Column chromatography of the foam (25 g SiO₂), eluting with ethyl acetate gave the title compound as a 1:1 mixture of diastereoisomers (417 mg, 70%), mp 115°–119° C.

Found: C,65.02; H,6.54; N,7.05%. C₃₃H₃₈ClN₃OS requires: C,66.93; H,6.47; N,7.10%.

δ (CDCl₃): 0.64 (3H,d,J=5 Hz), 0.74 (3H,d,J=5 Hz), 0.82 (6H,t,J=5 Hz), 1.05–1.70 (6H,m), 2.33 (1H,m), 2.47 (1H,m), 2.53 (3H,d,J=4 Hz), 2.60 (3H,d,J=4 Hz), 2.65–2.83 (5H,m), 3.0 (1H,dd,J=6,14 Hz), 3.15 (2H,d,J=7 Hz), 3.78 (6H,s), 3.98 (1H,d,J=12 Hz), 4.06 (2H,s), 4.08 (1H,d,J=12 Hz), 4.53 (1H,q,J=6 Hz), 4.65 (1H,q,J=7 Hz), 5.08 (1H,brm), 5.45 (1H,d,J=8 Hz), 5.58 (1H,brm), 5.94 (1H,d,J=8 Hz), 6.72 (1H,m), 6.81 (4H,t,J=8 Hz), 6.97 (5H,m), 7.1–7.3 (10H,m), 7.35 (2H,d,J=8 Hz), 7.64 (2H,t,J=8 Hz), 7.98 (1H,s) and 8.12 (1H,s).

DESCRIPTION 30

4-Methoxy-2-(4-methoxybenzylthio)-α-(2-methyl-propl)-N-(2-oxo-3-azacyclotridecyl)phenylpropanamide (D30)

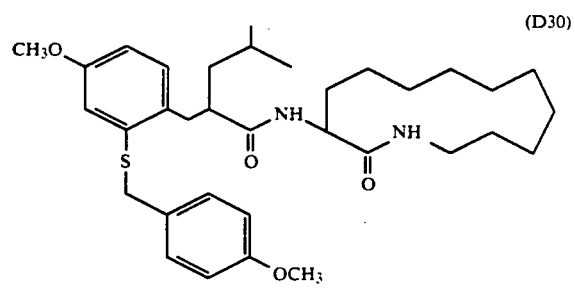

Reaction of 4-methoxy-2-(4-methoxybenzylthio)-α-(2-methylpropyl)phenylpropanoic acid (D17) (495 mg, 1.3 mmol) with N-ethyl-N'-dimethylaminopropylcarbodiimide (302 mg; 1.57 mmol) in dichloromethane (5 ml) followed by (—)-3-aminoazacyclotridecan-2-one (310 mg, 1.57 mmol) ([α]$_D^{20}$ = —63.6°/c = 1% in MeOH) by the procedure given for Description 8, gave the title compound (220 mg) as a 1:1 mixture of diastereoisomers, mp 138°–146° C. (ether-pentane).

Found: C,70.28; H,8.78; N,4.56%. $C_{34}H_{50}N_2O_4S$ requires C,70.07; H,8.65; N,4.81%.

δ (CDCl$_3$): 0.82 (3H,d,J = 8 Hz), 0.89 (3H,d,J = 8 Hz), 1.2–1.8 (21H,m), 2.5 (1H,m), 2.65–2.95 (3H,m), 3.6 (1H,m), 3.72 (s) and 3.74 (s) (total 3H), 3.79 (s) and 3.82 (s) (total 3H), 4.08 (2H,m), 4.30 (0.5H,m), 4.40 (0.5H,m), 6.05 (1H,m), 6.15 (0.5H,m), 6.25 (0.5H,m), 6.55 (1H,m) and 6.75–7.3 (6H,m).

EXAMPLE 1

2-Mercapto-N-[2-(4-methoxyphenyl)-1-(S)-(methylaminocarbonyl)ethyl]-α-(2-methylpropyl)phenyl-propanamide (E1)

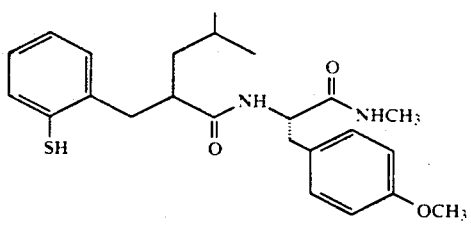

(E1)

Each of the Separated isomers of 2-benzylthio-N-[2-(4-methoxyphenyl)-1-(S)-(methylaminocarbonyl)ethyl]-α-(2-methylpropyl)phenylpropanamide (D3) were individually dissolved in liquid ammonia (5 ml) and were treated with small pieces of sodium until a blue colour persisted for two minutes. Solid ammonium chloride was added, and the ammonia was allowed to evaporate under a stream of nitrogen. The residual solid was partitioned between water and dichloromethane. The aqueous phase was extracted with dichloromethane, then the combined organics were washed successively with 1M hydrochloric acid, water and brine. The solution was dried (MgSO$_4$) and evaporated to leave a white solid which was triturated with ether.

Thus D3 (Isomer A, 74 mg) gave the title compound (Isomer A), 53 mg (87%), mp 160°–164° C. (Found: C,67.26; H,7.68; N,6.62. $C_{24}H_{32}N_2O_3S$ requires C,67.26; H,7.53; N,6.54%).

δ (CDCl$_3$): 0.88 (6H,t,J = 6 Hz), 1.2–1.35 (1H,m), 1.5–1.7 (2H,m), 2.48 (1H,dd,J = 13,8 Hz), 2.58 (1H,dd,J = 13,5 Hz), 2.65 (3H,d,J = 5 Hz), 2.7–2.9 (3H,m), 3.45 (1H,s), 3.77 (3H,s), 4.38 (1H,q,J = 7 Hz), 5.47 (1H,brs), 5.88 (1H,brd,J = 8 Hz), 6.77 (2H,d,J = 9 Hz), 6.93 (2H,d,J = 9 Hz) and 7.0–7.3 (5H,s).

and D3 (Isomer B, 160 mg) gave the title compound (Isomer B), 111 mg, 84%, mp 165°–168° C.

(Found: C,67.27; H,7.55; N,6.47. $C_{24}H_{32}N_2O_3S$ requires C,67.26; H,7.53; N,6.54%).

(CDCl$_3$): 0.75 (3H,d,J = 6 Hz), 0.81 (3H,d,J = 6 Hz), 1.10–1.25 (2H,m), 1.6 (m), 2.5 (1H,m), 2.57 (3H,d,J = 5 Hz), 2.68–3.05 (4H,m), 3.44 (1H,s), 3.78 (3H,s), 4.55 (1H,q,J = 8 Hz), 5.30 (brs), 5.52 (1H,brd,J = 9 Hz) and 6.75–7.25 (8H,m).

EXAMPLE 2

2-Mercapto-3-methoxy-N-2-(4-methoxyphenyl)-1-(S)-(methylaminocarbonyl)ethyl]-α-(2-methylpropyl)phenyl-propanamide (E2)

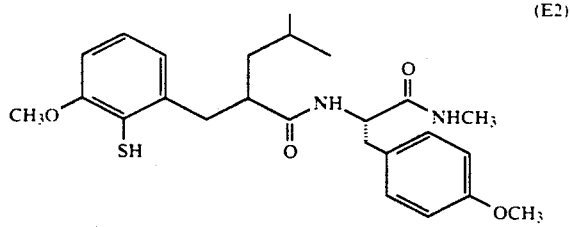

(E2)

Each of the isomers of 2-benzylthio-3-methoxy-N-[2-(4-methoxyphenyl)-1-(S)-(methylaminocarbonyl)ethyl]-α-(2-methylpropyl)phenylpropanamide (D8) were treated in the manner described in Example 1. Thus D8 (Isomer A, 100 mg) gave the title compound (Isomer A), 73 mg (88%), mp 156°–160° C.

(Found: C,65.51; H,7.39; N,6.00. $C_{25}H_{34}N_2O_4S$ requires C,65.47; H,7.47; N,6.11%).

δ (CDCl$_3$): 0.87 (6H,t,J = 7 Hz), 1.30 (1H,m), 1.60 (2H,m), 2.50 (1H,dd,J = 13,7 Hz), 2.63 (3H,d,J = 5 Hz), 2.63 (1H,m), 2.72–2.90 (3H,m), 3.78 (3H,s), 3.92 (3H,s), 4.33 (1H,s), 4.40 (1H,m), 5.50 (1H,brd), 5.79 (1H,d,J = 8 Hz), 6.75 (4H,m), 6.90 (2H,d,J = 9 Hz) and 7.01 (1H,t,J = 8 Hz).

and D8 (Isomer B, 100 mg) gave the title compound (Isomer B), 36 mg (43%), mp 171°–177° C. after column chromatography (10 g SiO$_2$) eluting with ethyl acetate.

(Found: C,65.81; H,7.43; N,5.82. $C_{25}H_{34}N_2O_4S$ requires: C,65.47; H,7.47; N,6.11%).

δ (CDCl$_3$): 0.74 (3H,d,J = 6 Hz), 0.80 (3H,d,J = 6 Hz), 1.13 (m), 1.55 (m), 2.42–2.60 (1H,m), 2.58 (3H,d,J = 5 Hz), 2.7–3.1 (4H,m), 3.77 (3H,s), 3.90 (3H,s), 4.30 (1H,s), 4.57 (1H,q,J = 7 Hz), 5.40 (2H,m), 6.71 (2H,m), 6.80 (2H,d,J = 8 Hz), 7.00 (1H,t,J = 8 Hz) and 7.04 (2H,d,J = 8 Hz).

EXAMPLE 3

2-Mercapto-4-methoxy-N-2-(4-methoxyphenyl)-1-(S)-(methylaminocarbonyl)ethyl]-α-(2-methylpropyl)-phenylpropanamide (E3)

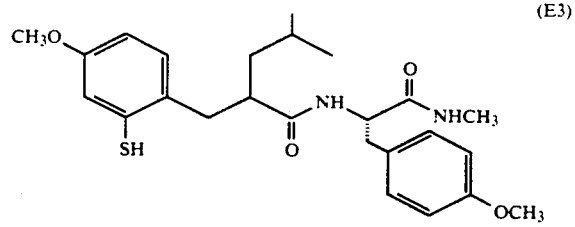

(E3)

4-Methoxy-2-(4-methoxybenzylthio)-N-[2-(4-methoxyphenyl-1-(S)-(methylaminocarbonyl)ethyl]-α-(2-methylpropyl)phenylpropanamide (D18) (181 mg, 0.31 mmol) was deprotected in a similar manner to that described in Example 4 to give the title compound as a 1:1 mixture of diastereoisomers (73 mg, 51%) mp 127°–139° C.

Found: C,65.70; H,7.19; N,5.84%. $C_{25}H_{34}N_2O_4S$ requires: 65.47; H,7.47; N,6.11%.

δ (CDCl$_3$): 0.75 (3H,d,J = 6 Hz), 0.81 (3H,d,J = 6 Hz), 0.88 (6H,t,J = 6 Hz), 1.1–1.35 (2H,m), 1.4–1.7 (4H,m), 2.4-2.95 (9H,m), 2.58 (3H,d,J=4 Hz), 2.66 (3H,d,J=4 Hz), 3.03 (1H,dd,J=6,16 Hz), 3.47 (1H,s), 3.49 (1H,s), 3.74 (3H,s), 3.75 (3H,s), 3.78 (6H,s), 4.40 (1H,m), 4.57 (1H,q,J=7 Hz), 5.30 (1H,brm), 5.50 (2H,brm), 5.90 (1H,d,J=8 Hz), 6.61 (2H,m), 6.73-6.85 (5H,m) and 6.90-7.08 (7H,m).

EXAMPLE 4

3-Trifluoromethyl-2-mercapto-N-[2-(4-methoxyphenyl)-1-(S)-(methylaminocarbonyl)ethyl]-α-(2-methylpropyl)phenylpropanamide (E4)

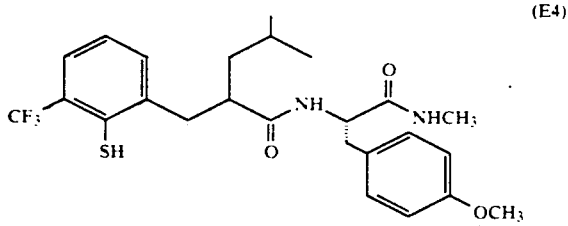

(E4)

An ice-cooled solution of 3-trifluoromethyl-2-(4-methoxybenzylthio)-N-[2-(4-methoxyphenyl)-1-(S)-(methylaminocarbonyl)ethyl]-α-(2-methylpropyl)phenylpropanamide (D13) (308 mg, 0.5 mmol) and anisole (0.1 ml) in trifluoroacetic acid (5 ml) was treated with mercuric acetate (160 mg, 0.5 mmol). After 15 min the solvent was evaporated and the residue was azeotroped dry with toluene. The residual oil was triturated with ether to give a white solid, which was separated and washed with a little ether. The solid was dissolved in dry DMF (3 ml) and the solution was purged with nitrogen. Hydrogen sulphide gas was bubbled through the solution for 3 min. The resulting black suspension was purged with nitrogen for 30 min, then the solvent was evaporated in vacuo. Column chromatography (10 g silica) eluting with ethyl acetate and trituration of the product with pentane gave the title compound as a 1:1 mixture of diastereoisomers (88 mg, 35%), mp 88°-102° C.

Found: C,60.30; H,6.08; N,5.55%. $C_{25}H_{31}F_3N_2O_5S$ requires C,60.46; H,6.29; N,5.64%.

δ (CDCl₃): 0.77 (3H,d,J=6 Hz), 0.83 (3H,d,J=6 Hz), 0.88 (3H,d,J=6 Hz), 0.90 (3H,d,J=6 Hz), 1.1-1.8 (6H,m), 2.44-2.65 (3H,m), 2.59 (3H,d,J=4 Hz), 2.67 (3H,d,J=4 Hz), 2.7-3.1 (7H,m), 4.78 (6H,s), 4.00 (2H,2xs), 4.42 (1H,m), 4.50 (1H,q,J=7 Hz), 5.42 (2H,brm), 5.73 (1H,d,J=7 Hz), 5.98 (1H,d,J=7 Hz), 6.75-6.9 (6H,m), 7.05-7.18 (4H,m), 7.23-7.35 (2H,m) and 7.54 (2H,m).

EXAMPLE 5

4-Chloro-2-mercapto-N-[2-(4-methoxyphenyl)-1-(S)-(methylaminocarbonyl)ethyl]-α-(2-methylpropyl)phenylpropanamide (E5)

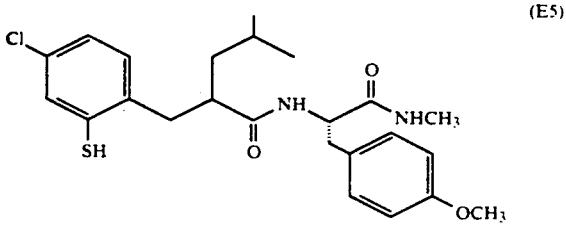

(E5)

4-Chloro-2-(4-methoxybenzylthio)-N-[2-(4-methoxyphenyl)-1-(S)-(methylaminocarbonyl)ethyl]-α-(2-methylpropyl)phenylpropanamide (D23) (170 mg, 0.29 mmol) was deprotected in a similar manner to that described in Example 4 to give the title compound as a 1:1 mixture of diastereoisomers (92 mg, 69%) mp 174°-178° C.

Found: C,62.44; H,6.74; N,6.02%. $C_{24}H_{31}ClN_2O_3S$ requires: C,62.25; H,6.75; N,6.05%.

δ (CDCl₃): 0.78 (3H,d,J=6 Hz), 0.83 (3H,d,J=6 Hz), 0.88 (6H,t,J=6 Hz), 1.1-1.35 (2H,m), 1.45-1.7 (4H,m), 2.40-3.0 (10H,m), 2.62 (3H,d,J=4 Hz), 2.66 (3H,d,J=4 Hz), 3.52 (2H,s), 3.78 (3H,s), 3.80 (3H,s), 4.40 (1H,q,J=6 Hz), 4.50 (1H,q,J=7 Hz), 5.28 (1H,brs), 5.46 (1H,brs), 5.66 (1H,d,J=8 Hz), 6.0 (1H,d,J=8 Hz), 6.75-6.83 (4H,m), 6.9-7.1 (8H,m) and 7.28 (2H,m).

EXAMPLE 6

2-Mercapto-4methyl-N-[2-(4-methoxyphenyl)-1-(S)-(methylaminocarbonyl)ethyl]-α-(2-methylpropyl)-phenylpropanamide (E6)

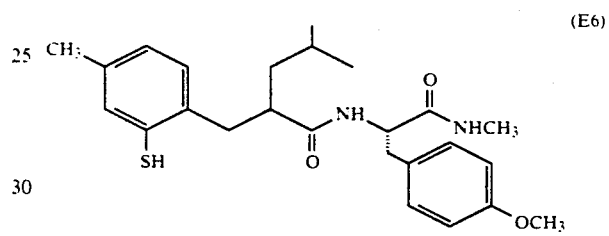

(E6)

The title compound is prepared using an analogous procedure to that described in Example 1.

EXAMPLE 7

2-Chloro-6-mercapto-N-[2-(4-methoxyphenyl)-1-(S)-(methylaminocarbonyl)ethyl]-α-(2-methylpropyl)-phenylpropanamide (E7)

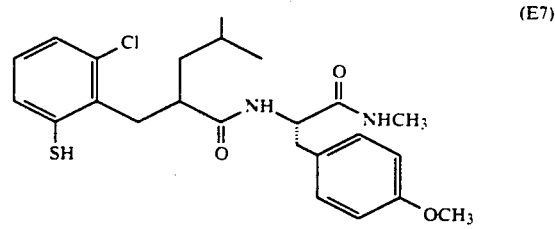

(E7)

2-Chloro-6-(4-methoxybenzylthio)-N-[2-(4-methoxyphenyl)-1-(S)-(methylaminocarbonyl)ethyl]-α-(2-methylpropyl)phenylpropanamide (D28) (400 mg, 0.68 mmol) was deprotected in a similar manner to that described in Example 4 to give the title compound as a 1:1 mixture of diastereoisomers (228 mg, 72%), mp 159°-163° C.

δ (CDCl₃): 0.72 (3H,d,J=5 Hz), 0.82 (3H,d,J=5 Hz), 0.84 (3H,d,J=6 Hz), 0.88 (3H,d,J=6 Hz), 1.1-1.35 (2H,m), 1.40-1.85 (4H,m), 2.55-3.05 (8H,m), 2.63 (3H,d,J=4 Hz), 2.66 (3H,d,J=4 Hz), 3.1-3.25 (2H,m), 3.77 (6H,s), 4.02 (1H,s), 4.07 (1H,s), 4.43 (1H,m), 4.55 (1H,q,J=7 Hz), 5.55 (2H,brs), 5.70 (1H,d,J=8 Hz), 5.95 (1H,d,J=8 Hz), 6.75-6.83 (4H,m), 6.95-7.12 (6H,m) and 7.15-7.23 (4H,m).

EXAMPLE 8

4-Chloro-2-mercapto-N-[2-(3-indolyl)-1-(S)-(methyl-aminocarbonyl)ethyl]-α-(2-methylpropyl)phenyl-propanamide (E8)

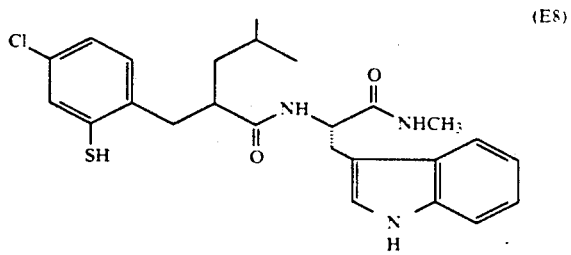

4-Chloro-2-(4-methoxybenzylthio)-N-[2-(3-indolyl)-1-(S)-(methylaminocarbonyl)ethyl]-α-(2-methylpropyl)-phenylpropanamide (D29) (140 mg, 0.24 mmol) was deprotected in a similar manner to that described in Example 4 to give the title compound as a 1:1 mixture of diastereoisomers (32 mg, 29%), mp 75°-78° C.

δ (CDCl₃): 0.75 (3H,d,J=6 Hz), 0.82 (3H,d,J=6 Hz), 0.88 (6H,m), 1.27 (4H,m), 1.60 (2H,m), 2.56 (3H,d,J=4 Hz), 2.61 (3H,d,J=4 Hz), 2.80 (4H,m), 3.15 (2H,m), 3.47 (1H,m), 3.78 (1H,m), 4.56 (2H,m), 5.23 (1H,brs), 5.46 (1H,brs), 5.80 (1H,d,J=7 Hz), 6.10 (1H,d,J=7 Hz), 6.80 (2H,m), 6.98 (4H,m), 7.17 (8H,m), 7.36 (1H,d,J=7 Hz), 7.65 (1H,d,J=7 Hz) and 8.15 (2H,brd).

EXAMPLE 9

2-Mercapto-4-methoxy-α-(2-methylpropyl)-N-(2-oxo-3-azacyclotridecyl)phenylpropanamide (E9)

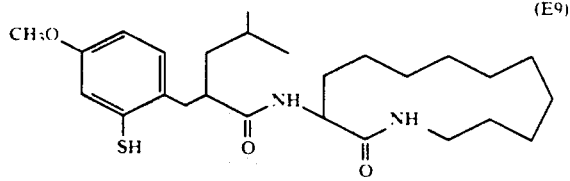

The compound of Description 30 was deprotected with sodium and liquid ammonia in a similar manner to that described in Example 1 to give the title compound as a 1:1 mixture of diastereoisomers, mp. 131°-136° C. (after trituration with pentane).

EXAMPLE 10

2-Mercapto-α-(2-methylpropyl)-N-(2-oxo-3-azacyclo-tridecyl)phenylpropanamide (E10)

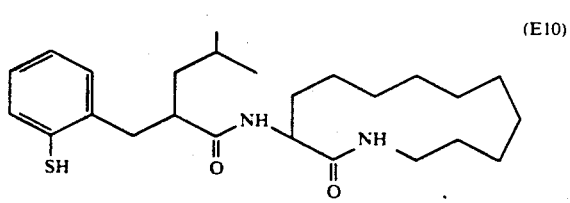

The title compound was prepared as a 1:1 mixture diastereoisomers from the compound of Description 2 using procedures described in Description 30 and Example 1, mp 166°-171° C. (after trituration with diethyl ether followed by pentane).

EXAMPLE 11

3-Chloro-2-mercapto-N-2-(4-methoxyphenyl)-1-(S)-(methylaminocarbonyl)ethyl]-α-(2-methylpropyl)-phenylpropanamide (E11)

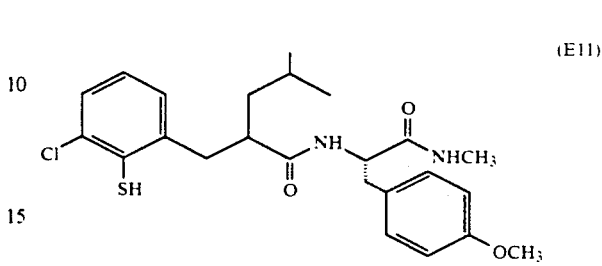

The title compound was prepared as a 1:1 mixture of diastereoisomers from 3-chloro-2-(4-methoxybenzylthio)-N-[2-(4-methoxyphenyl)-1-(S)-(methylaminocarbonyl)ethyl]-α-(2-methylpropyl)phenylpropanamide in a similar manner to that described in Example 4, mp 68°-74° C. (after trituration with hexane).

EXAMPLE 12

3-Chloro-2-mercapto-α-(2-methylpropyl)-N-(2-oxo-3-azacyclotridecyl)phenylpropanamide (E12)

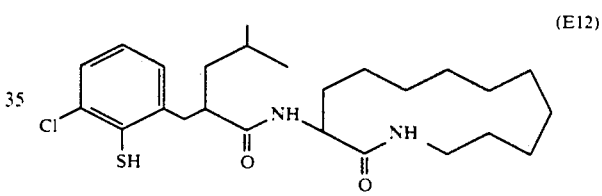

The title compound was prepared as a 1:1 mixture of diastereoisomers from 3-chloro-2-(4-methoxybenzylthio)-α-(2-methylpropyl)-N-(2-oxo-3-azacylotridecyl)-phenylpropanamide in a similar manner to that described in Example 4, mp 143°-148° C. (after trituration with hexane).

EXAMPLE 13

Di-[2-(2-((2-(4-methoxyphenyl)-1-(S)-(methylaminocar-bonyl)ethyl)aminocarbonyl)-4-methylpentyl)phenyl]di-sulphide (E13)

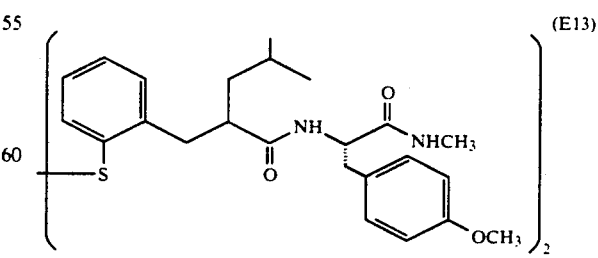

The title compound was prepared from the compound of Example 1B by oxidative coupling in methanol in the presence of iodine, mp 193°-197° C.

EXAMPLE 14

2-Mercapto-N-[2-(4-methoxyphenyl)-1-(S)-(methylaminocarbonyl)ethyl]-α-(2-methylpropyl)phenylbutanamide (E14)

(E14)

The title compound is prepared from 2-(tert-butylthio)-N-[2-(4-methoxyphenyl)-1-(S)-(methylaminocarbonyl)ethyl]-α-(2-methylpropyl)phenylbutanamide in a similar manner to that described in Example 4.

COLLAGENASE INHIBITOR ASSAY

The test is performed essentially as in Cawston and Barrett, Anal. Biochem. 99, 340–345 (1979). Compounds for testing are dissolved in methanol and added to collagenase (purified from cultures of rabbit bone or from culture supernatants from the human lung fibroblast cell line, WI-38) in buffer. In order to ensure that thiol collagenase inhibitors remained unoxidised, β-mercaptoethanol may be incorporated in the methanol solvent and/or the diluent buffers. The minimal direct effect of β-mercaptoethanol on the degradation of collagen by human or rabbit collagenase is controlled for. After a 5–15 min pre-incubation at 37° C., the assay tubes are cooled to 4° C. and $^{14}$C-acetylated rat skin Type II collagen is added. The assay tubes are incubated at 37° C. overnight. The $^{14}$C-collagen forms insoluble fibrils which are the substrate for the enzyme.

To terminate the assay, the assay tubes are spun at 12000 rpm for 15 min. Undigested $^{14}$C-collagen is pelleted, while digested $^{14}$C-collagen is found as soluble peptides in the supernatant. A sample of the supernatant is taken for liquid scintillation counting.

The activity of collagenase inhibitors ($IC_{50}$: 50% inhibitory concentration) is expressed as that concentration of compound that inhibits a known (standard) concentration of enzyme by 50%.

The activities of representative compounds of the invention, in the above test procedure, are illustrated in the table below:

| Example No | Isomer | $IC_{50}$ (μm) |
|---|---|---|
| Inhibition of rabbit bone collagenase | | |
| 1 | A | 1.9 |
| 1 | B | 1.4 |
| Inhibition of human lung fibroblast collagenase | | |
| 1 | B | 0.71 |
| | | 0.024* |
| 5 | mixture of diastereoisomers | 1.8 |
| | | 0.25* |
| 8 | mixture of diastereoisomers | 1.5 |
| | | 0.19* |

* = + β-mercaptoethanol

I claim:

1. A compound of formula (I), or a salt, solvate, or hydrate thereof:

(I)

in which:

$R_1$ and $R_2$ are independently hydrogen; alkyl; alkoxy; halogen; or $CF_3$;

$R_3$ is hydrogen;

$$-\overset{O}{\underset{\|}{C}}-alkyl \text{ or } -\overset{O}{\underset{\|}{C}}-Z,$$

where Z is aryl substituted with —OH, $C_{1-6}$ alkyl, $C_{1-6}$ alkoxy, or halogen; or a group R—S— where R is $C_{1-6}$ alkyl or an organic residue such that the compound of formula (I) is a dimer about the disulfide bond;

$R_4$ is $C_{3-6}$ alkyl;

$R_5$ is hydrogen; alkyl; —$CH_2$—$R_{10}$ where $R_{10}$ is phenyl or heteroaryl optionally substituted with OH, $C_{1-6}$ alkyl, $C_{1-6}$ alkoxy, or halogen and where $R_{10}$ is heteroaryl it is selected from 5- and 6-membered monocyclic and 9- or 10-membered bicyclic heteroaryls containing one or two heteroatoms selected from oxygen, nitrogen, and sulfur;

or a group $$-\underset{R_{12}}{\overset{|}{CH}}-O-R_{11}$$

where $R_{11}$ is hydrogen; alkyl; or —$CH_2$—Ph where Ph is phenyl optionally substituted with —OH, $C_{1-6}$ alkyl, $C_{1-6}$ alkoxy, or halogen; and $R_{12}$ is hydrogen or alkyl; and $R_6$ is hydrogen; alkyl; or a group $$-\underset{R_{13}}{\overset{|}{CH}}-COR_{14}$$

where $R_{13}$ is hydrogen; or alkyl; and $R_{14}$ is hydroxy; alkoxy; or —$NR_{7a}R_8$ where each of $R_{7a}$ and $R_8$ is hydrogen or alkyl, or $R_{7a}$ and $R_8$ together with the nitrogen atom to which they are bonded form a 5-, 6-, or 7-membered ring with an optional oxygen, sulphur or nitrogen atom in the ring;

or $R_5$ and $R_6$ are joined together as —$(CH_2)_m$— where m is an integer from 4 to 12;

X is $(CH_2)_n$ where n is 0, 1, or 2; and Y is $CH_2$.

2. A compound according to claim 1 in which $R_1$ and $R_2$ are independently hydrogen, $C_{1-4}$ alkyl, $C_{1-4}$ alkoxy, halogen or trifluoromethyl.

3. A compound according to claim 1 in which $R_3$ is hydrogen, acetyl, benzoyl, or a group R—S— where R is an organic residue such that the compound of formula (I) is a dimer about the disulphide bond, or R is $C_{1-6}$ alkyl.

4. A compound according to claim 1 in which $R_4$ is n-butyl, iso-butyl or sec-butyl.

5. A compound according to claim 1 in which $R_5$ is iso-butyl, benzyl, 4-methoxybenzyl, 1-(benzyloxy)ethyl or 3-indolylmethyl.

6. A compound according to claim 1 in which $R_6$ is hydrogen, methyl, ethyl, or 1-(methoxycarbonyl)ethyl.

7. A compound according to claim 1 in which $R_5$ and $R_6$ are joined together as $-(CH_2)_m$, where $m=10$.

8. A compound according to claim 1 in which n is O.

9. A compound according to claim 1 in which $R_1$ and $R_2$ are independently hydrogen, methyl, methoxy, chloro or trifluoromethyl; $R_3$ is hydrogen or 2-(2-((2-(4-methoxyphenyl)-1-(S)-(methylaminocarbonyl)ethyl)aminocarbonyl)-4-methylpentyl)phenyl thio; $R_4$ is iso-butyl; $R_5$ is 4-methoxybenzyl or 3-indolymethyl; and $R_6$ is methyl; or $R_5$ and $R_6$ are joined together as $-(CH_2)_m-$ where $m=10$; and n is O or 1.

10. A compound according to claim 1 in which the chiral centre marked with an asterisk in formula (I) has the S-configuration.

11. A compound selected from the group consisting of:

2-mercapto-N-[2-(4-methoxyphenyl)-1-(S)-(methylamino-carbonyl)ethyl]-α-(2-methylpropyl)-phenylpropanamide;

2-mercapto-3-methoxy-N-[2-(4-methoxyphenyl)-1-(S)-(methylaminocarbonyl)ethyl]-α-(2-methylpropyl)-phenylpropanamide;

2-mercapto-4-methoxy-N-[2-(4-methoxyphenyl)-1-(S)-(methylaminocarbonyl)ethyl]-α-(2-methylpropyl)-phenylpropanamide;

3-trifluoromethyl-2-mercapto-N-[2-(4-methoxyphenyl)-1-(S)-(methylaminocarbonyl)ethyl]-α-(2-methylpropyl)phenylpropanamide;

4-chloro-2-mercapto-N-[2-(4-methoxyphenyl)-1-(S)-(methylaminocarbonyl)ethyl]-α-(2-methylpropyl)-phenylpropanamide;

2-mercapto-4-methyl-N-[2-(4-methoxyphenyl)1-(S)-(methylaminocarbonyl)ethyl]-α-(2-methylpropyl)-phenylpropanamide;

2-chloro-6-mercapto-N-[2-(4-methoxyphenyl)1-(S)-(methylaminocarbonyl)ethyl]-α-(2-methylpropyl)-phenylpropanamide;

4-chloro-2-mercapto-N-[2-(3-indolyl)-1-(S)-(methylaminocarbonyl)ethyl]-α-(2-methylpropyl)-phenylpropanamide;

2-mercapto-4-methoxy-α-(2-methylpropyl)-N-(2-oxo-3-azacyclotridecyl)phenylpropanamide;

2-mercapto-α-(2-methylpropyl)-N-(2-oxo-3-azacyclotridecyl)phenylpropanamide;

3-chloro-2-mercapto-N-[2-(4-methoxyphenyl)-1-(S)-(methylaminocarbonyl)ethyl]-α-(2-methylpropyl)-phenylpropanamide;

3-chloro-2-mercapto-α-(2-methylpropyl)-N-(2-oxo-3-azacyclotridecyl)phenylpropanamide;

di-[2-(2-((2-(4-methoxyphenyl)-1-(S)-(methylaminocarbonyl)ethyl)aminocarbonyl)-4-methylpentyl)-phenyl]disulphide; and 2-mercapto-N-[2-(4-methoxyphenyl)-1-(S)-(methylaminocarbonyl)ethyl]-α-(2-methylpropyl)-phenylbutanamide.

12. A pharmaceutically acceptable salt, solvate or hydrate of a compound according to claim 1.

13. A pharmaceutical composition comprising a compound of formula (I) as defined in claim 1, or a pharmaceutically acceptable salt, solvate or hydrate thereof, and a pharmaceutically acceptable carrier.

14. A method of treating collagenolytic conditions in mammals which comprises administering an effective amount of a compound of formula (I) as defined in claim 1 or a pharmaceutically acceptable salt, solvate or hydrate thereof to a sufferer.

* * * * *